(12) United States Patent
Eroshenko et al.

(10) Patent No.: US 11,473,090 B2
(45) Date of Patent: Oct. 18, 2022

(54) LINEAR COVALENTLY CLOSED VECTORS AND RELATED COMPOSITIONS AND METHODS THEREOF

(71) Applicant: Helix Nanotechnologies, Inc., Walnut, CA (US)

(72) Inventors: Nikolai Eroshenko, Boston, MA (US); Nikhil Dhar, Boston, MA (US)

(73) Assignee: Helix Nanotechnologies, Inc., Walnut, CA (US)

(*) Notice: Subject to any disclaimer, the term of this patent is extended or adjusted under 35 U.S.C. 154(b) by 319 days.

(21) Appl. No.: 16/614,101

(22) PCT Filed: May 16, 2018

(86) PCT No.: PCT/US2018/032988
§ 371 (c)(1),
(2) Date: Nov. 15, 2019

(87) PCT Pub. No.: WO2018/213460
PCT Pub. Date: Nov. 22, 2018

(65) Prior Publication Data
US 2020/0172914 A1    Jun. 4, 2020

Related U.S. Application Data

(60) Provisional application No. 62/507,144, filed on May 16, 2017.

(51) Int. Cl.
| | | |
|---|---|---|
| *C12Q 1/68* | (2018.01) | |
| *C12N 15/66* | (2006.01) | |
| *C12N 15/63* | (2006.01) | |
| *C12Q 1/6844* | (2018.01) | |
| *C12Q 1/6897* | (2018.01) | |

(52) U.S. Cl.
CPC ............. *C12N 15/66* (2013.01); *C12N 15/63* (2013.01); *C12Q 1/6846* (2013.01); *C12Q 1/6897* (2013.01)

(58) Field of Classification Search
CPC ....................................................... C12Q 1/68
USPC ....................................................... 435/6.12
See application file for complete search history.

(56) References Cited

U.S. PATENT DOCUMENTS

| | | | |
|---|---|---|---|
| 2008/0153763 A1* | 6/2008 | Takagi | C12N 15/111 536/24.5 |
| 2013/0203123 A1* | 8/2013 | Nelson | C12Q 1/6869 435/91.52 |
| 2016/0040227 A1* | 2/2016 | Mir | G01N 21/6428 506/4 |

(Continued)

FOREIGN PATENT DOCUMENTS

WO    WO-2016/195598 A1    12/2016

OTHER PUBLICATIONS

International Search Report for PCT/US2018/032988 (Linear Covalently Closed Vectors and Related Compositions and Methods Thereof, filed May 16, 2018), issued by ISA/USA, 4 pages (dated Aug. 29, 2018).

(Continued)

*Primary Examiner* — Aaron A Priest
(74) *Attorney, Agent, or Firm* — Choate, Hall & Stewart LLP; Stephanie L. Schonewald; Mandeep Kaur

(57) ABSTRACT

Linear covalently closed vectors, and compositions and methods for making same.

8 Claims, 7 Drawing Sheets

Specification includes a Sequence Listing.

(56) References Cited

U.S. PATENT DOCUMENTS

2016/0304948 A1* 10/2016 Lee .................... C12Q 1/6855
2017/0088887 A1   3/2017 Makarov et al.

OTHER PUBLICATIONS

Jiang, X. et al., Advanced Design of Dumbbell-Shaped Genetic Minimal Vectors Improves Non-coding and Coding RNA Expression, Molecular Therapy, 24(9): 1581-1591 (2016).
Written Opinion for PCT/US2018/032988 (Linear Covalently Closed Vectors and Related Compositions and Methods Thereof, filed May 16, 2018), issued by ISA/USA, 11 pages (dated Aug. 29, 2018).
Yu, H. et al., Efficient production of superior dumbbell-shaped DNA minimal vectors for small hairpin RNA expression, Nucleic Acids Research, 43(18): e120 (2015).

* cited by examiner

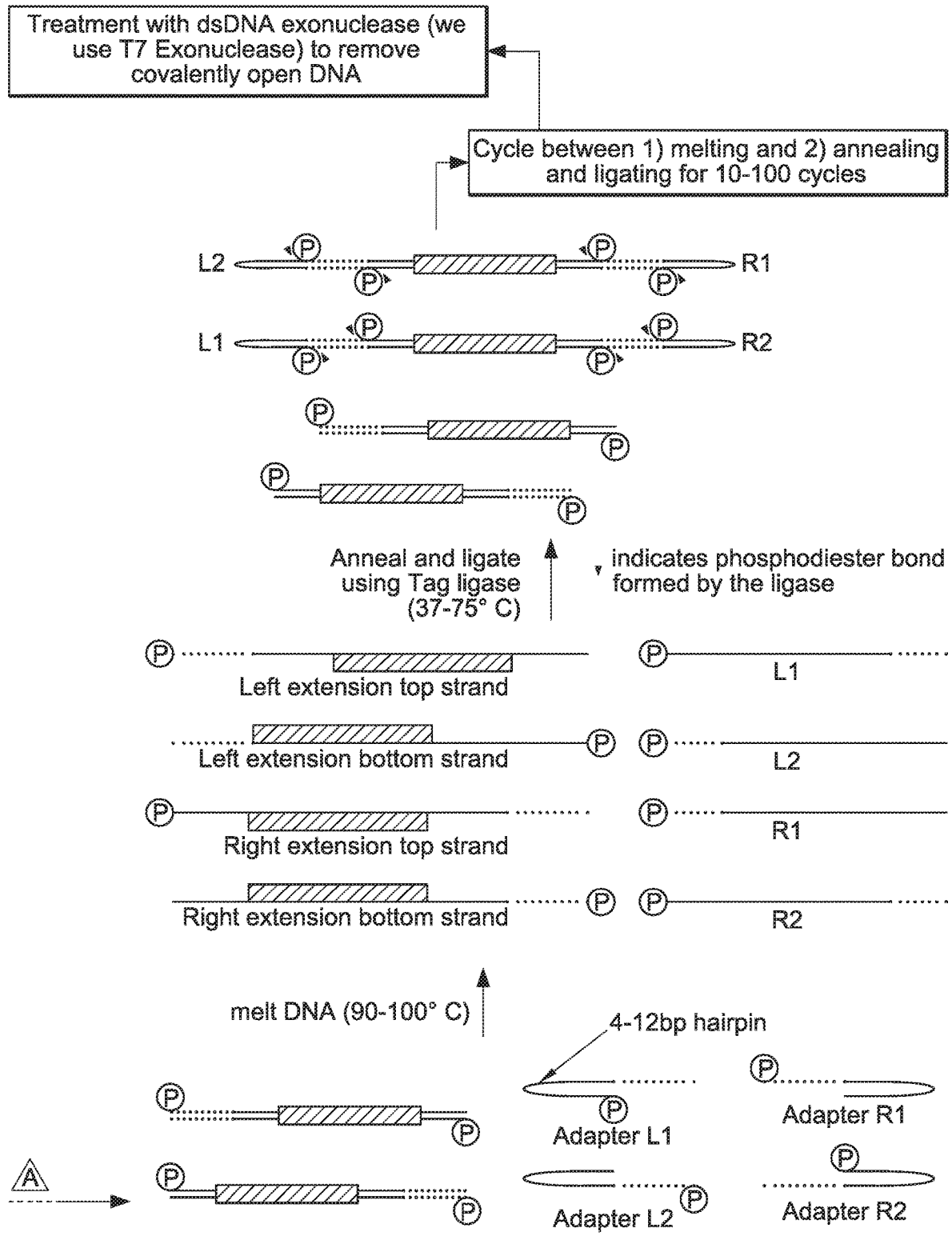
FIG. 2 contd.

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgctgcttcg cgatgtacgg g                                                    21

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgtcggttag ctcgctcagc tgatgcgctg cttcgcgatg tacggg                         46

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
ctgagtagtg cgcgagcaaa atttaagcta caac                          34

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtcggttag ctcgctcagc tgatgctgag tagtgcgcga gcaaaattta agctacaac    59

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agaagtggtc ctgcaacttt atccgcc                                  27

<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtcggttag ctcgctcagc tgatgagaag tggtcctgca actttatccg cc          52

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagcacagaa aagcatctta cttggcatga cag                           33

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccctatgggt cggcgcaatg ccagcacaga aaagcatctt acttggcatg acag        54

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
catcagctga gcgagctaac cgacactgcg gtccaactca ggcgtagacc tcctgtatgt    60
tcggaggtct acgcctgagt tggaccgcag                                     90

<210> SEQ ID NO 10
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagcgcgcaa cagcctacct tctcggacct atctaccgag aaggtaggct gttgcgcgct    60
gtgtcggtta gctcgctcag ctgatg                                         86

<210> SEQ ID NO 11
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcattgcgcc gacccatagg gctaacgaag gcgcccggta cggcattacc catctgccgt    60
accgggcgcc ttcgttag                                                  78

<210> SEQ ID NO 12
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgtcggagtg cggatcgaac ctggctaagt aggtgccagg ttcgatccgc actccgacgc    60
cctatgggtc ggcgcaatgc                                                80

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttaaggtacg ggaggtactt g                                              21

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtcggttag ctcgctcagc tgatgttaag gtacgggagg tacttg                   46

<210> SEQ ID NO 15

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgggttgaag gctctcaag                                                  19

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccctatgggt cggcgcaatg ctgggttgaa ggctctcaag                            40

<210> SEQ ID NO 17
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catcagctga gcgagctaac cgacactgcg gtccaactca ggcgtagacc tcctgtatgt      60
tcggaggtct acgcctgagt tggaccgcag                                      90

<210> SEQ ID NO 18
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagcgcgcaa cagcctacct tctcggacct atctaccgag aaggtaggct gttgcgcgct      60
gtgtcggtta gctcgctcag ctgatg                                          86

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcattgcgcc gacccatagg gctaacgaag gcgcccggta cggcattacc catctgccgt      60
accgggcgcc ttcgttag                                                   78

<210> SEQ ID NO 20
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```

```
cgtcggagtg cggatcgaac ctggctaagt aggtgccagg ttcgatccgc actccgacgc    60
cctatgggtc ggcgcaatgc                                                80
```

LINEAR COVALENTLY CLOSED VECTORS AND RELATED COMPOSITIONS AND METHODS THEREOF

CROSS-REFERENCE TO RELATED APPLICATIONS

This application is a national stage filing under U.S.C. § 371 of PCT International Application No. PCT/US2018/032988 filed May 16, 2018, which claims the benefit of and priority to U.S. provisional patent application serial number 62/507,144, filed May 16, 2017, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 18, 2018, is named 2012611-0009_SL.txt and is 5,498 bytes in size.

BACKGROUND

Linear, covalently close dumb-bell shaped vectors (typically referred to as 1 cc vectors) offer advantages over traditional plasmid vectors. For example, 1 cc vectors typically contain minimal sequences—e.g., sequence to be delivered as part of non-viral gene therapies and may exclude other sequences that are not intended to be expressed in target cells or tissues, e.g., bacterial genes, selection markers, origins of replication, etc.

SUMMARY

The present disclosure encompasses a recognition that current methods for producing 1 cc vectors are inefficient and/or often require use of chemically modified DNA, expensive enzymes, or bacterial systems. For example, the present disclosure encompasses a recognition that methods based on ligation of short overhangs are often limited in efficiency by the overhang length, that methods based on proto-telomerase enzymes require addition of unnecessary and possibly immunogenic bacterial sequences, and that methods based on nickases are limited by enzyme efficiency.

The present disclosure provides, among other things, linear covalently closed (1 cc) nucleic acid vectors and related compositions and methods. Provided compositions and methods facilitate efficient, scalable production of 1 cc nucleic acid vectors (e.g., 1 cc DNA vectors) that are not limited with respect to sizes in the same manner as are 1 cc vectors produced by prior art methods. Provided compositions also do not require the addition of bacterial sequences.

In some aspects, compositions useful in the generation of 1 cc nucleic acid vectors are provided.

In certain embodiments, provided are compositions comprising: (i) a first payload oligonucleotide including a first payload sequence and a first 3' extension sequence; (ii) a second payload oligonucleotide including a second payload sequence and a second 3' extension sequence, wherein the first payload sequence is complementary to the second payload sequence; (iii) a first adaptor oligonucleotide comprising: (a) a first stem sequence and a second stem sequence, wherein the first stem sequence is an inverted complement of the second stem sequence, and (b) a first adaptor 3' extension sequence that is complementary to the first 3' extension sequence; and (iv) a second adaptor oligonucleotide comprising: (a) a third stem sequence and a fourth stem sequence, wherein the third stem sequence is an inverted complement of the fourth stem sequence, and (b) a second adaptor 3' extension sequence that is complementary to the second 3' extension sequence.

In some embodiments, a first 3' extension sequence is 10 to 40 nucleotides in length. In some embodiments, a first adaptor 3' extension sequence is 10 to 40 nucleotides in length. In some embodiments, a second 3' extension sequence is 10 to 40 nucleotides in length. In some embodiments, a second adaptor 3' extension sequence is 10 to 40 nucleotides in length.

In some embodiments, a first 3' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a first 3' extension sequence can be at most 200, at most 150, at most 125, at most 110, at most 100, at most 90, at most 80, at most 70, at most 60, at most 50, at most 40, or at most 30 nucleotides in length. In some embodiments, a second 3' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a second 3' extension sequence can be at most 200, at most 150, at most 125, at most 110, at most 100, at most 90, at most 80, at most 70, at most 60, at most 50, at most 40, or at most 30 nucleotides in length.

In some embodiments, a first adaptor 3' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a first adaptor 3' extension sequence can be at most 200, at most 150, at most 125, at most 110, at most 100, at most 90, at most 80, at most 70, at most 60, at most 50, at most 40, or at most 30 nucleotides in length. In some embodiments, a second adaptor 3' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a second adaptor 3' extension sequence can be at most 200, at most 150, at most 125, at most 110, at most 100, at most 90, at most 80, at most 70, at most 60, at most 50, at most 40, or at most 30 nucleotides in length.

In certain embodiments, provided are compositions comprising: (i) a first payload oligonucleotide including a first payload sequence and a first 5' extension sequence; (ii) a second payload oligonucleotide including a second payload sequence and a second 5' extension sequence, wherein the first payload sequence is complementary to the second payload sequence; (iii) a first adaptor oligonucleotide comprising: (a) a first stem sequence and a second stem sequence, wherein the first stem sequence is an inverted complement of the second stem sequence, and (b) a first adaptor 5' extension sequence that is complementary to the first 5' extension sequence; and (iv) a second adaptor oligonucleotide comprising: (a) a third stem sequence and a fourth stem sequence, wherein the third stem sequence is an inverted complement of the fourth stem sequence, and (b) a second adaptor 5' extension sequence that is complementary to the second 5' extension sequence.

In some embodiments, a first 5' extension sequence is 10 to 40 nucleotides in length. In some embodiments, a first adaptor 5' extension sequence is 10 to 40 nucleotides in length. In some embodiments, a second 5' extension sequence is 10 to 40 nucleotides in length. In some embodiments, a second adaptor 5' extension sequence is 10 to 40 nucleotides in length.

In some embodiments, a first 5' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a first 5' extension sequence can be at most 200, at most 150, at most 125, at most 110, at most 100, at most 90, at most 80, at most 70, at most 60, at most 50, at most 40, or at most 30 nucleotides in length. In some embodiments, a second 5' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a second 5' extension sequence can be at most 200, at most 150, at most 125, at most 110, at most 100, at most 90, at most 80, at most 70, at most 60, at most 50, at most 40, or at most 30 nucleotides in length.

In some embodiments, a first adaptor 5' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a first adaptor 5' extension sequence can be at most 200, at most 150, at most 125, at most 110, at most 100, at most 90, at most 80, at most 70, at most 60, at most 50, at most 40, or at most 30 nucleotides in length. In some embodiments, a second adaptor 5' extension sequence can be at least 5, at least 10, at least 15, at least 20, at least 25, at least 30, at least 35, at least 40, at least 45, at least 50, at least 60, at least 70, at least 80, or at least 90 nucleotides in length. In some embodiments, a second adaptor 5' extension sequence can be at most 200, at most 150, at most 125, at most 110, at most 100, at most 90, at most 80, at most 70, at most 60, at most 50, at most 40, or at most 30 nucleotides in length.

In some embodiments, a composition comprises a molar excess of each of a first and a second adaptor oligonucleotides relative to a first and a second payload oligonucleotides. In some embodiments, a composition comprises at least a two-fold molar excess, at least a three-fold molar excess, at least a four-fold molar excess, at least a five-fold molar excess, at least a six-fold molar excess, at least a seven-fold molar excess, at least an eight-fold molar excess, at least a nine-fold molar excess, or at least a ten-fold molar excess of at least one of a first and a second adaptor oligonucleotides relative to a first and a second payload oligonucleotides.

In some embodiments, a composition comprises at least a two-fold molar excess, at least a three-fold molar excess, at least a four-fold molar excess, at least a five-fold molar excess, at least a six-fold molar excess, at least a seven-fold molar excess, at least an eight-fold molar excess, at least a nine-fold molar excess, or at least a ten-fold molar excess of both a first and a second adaptor oligonucleotides relative to a first and a second payload oligonucleotides.

In some embodiments, a first and/or a second adaptor oligonucleotide comprises a chemical modification. In some embodiments, the chemical modification is a modified nucleotide, e.g., a synthetic nucleotide.

In some embodiments, a first and/or a second adaptor oligonucleotide comprises a label, e.g., a purification label or a detectable label.

In some embodiments, a first and/or a second adaptor oligonucleotides is associated with a cell-penetrating peptide.

In some embodiments, a first and/or a second adaptor oligonucleotide is associated with a polyamide.

In some embodiments, a first and/or a second adaptor oligonucleotide is associated with an antigen-specific targeting ligand.

In some embodiments, a first and/or a second adaptor oligonucleotide is associated with a nuclear localization sequence peptide.

In some embodiments, a first and/or a second adaptor oligonucleotide includes at least 20 nucleotides.

In some embodiments, (i) a first payload sequence is hybridized to a second payload sequence; (ii) (a) a first adaptor 3' extension sequence is hybridized to a first 3' extension sequence or (b) a first adaptor 5' extension sequence is hybridized to a first 5' extension sequence; and (iii) (a) a second adaptor 3 extension sequence is hybridized to a second 3' extension sequence or (b) a second adaptor 5' extension sequence is hybridized to a second 5' extension sequence.

In some embodiments, a first stem sequence and a second stem sequence are 2 to 40 nucleotides in length. In some embodiments, a third stem sequence and a fourth stem sequence are 2 to 40 nucleotides in length In some embodiments, a first stem sequence and a second stem sequence are 4 to 40 nucleotides in length. In some embodiments, a third stem sequence and a fourth stem sequence are 4 to 40 nucleotides in length. In some embodiments, a first stem sequence and a second stem sequence are 5 to 40 nucleotides in length. In some embodiments, a third stem sequence and a fourth stem sequence are 5 to 40 nucleotides in length. In some embodiments, a first stem sequence and a second stem sequence are 8 to 40 nucleotides in length. In some embodiments, a third stem sequence and a fourth stem sequence are 8 to 40 nucleotides in length. In some embodiments, a first stem sequence and a second stem sequence are 10 to 40 nucleotides in length. In some embodiments, a third stem sequence and a fourth stem sequence are 10 to 40 nucleotides in length.

In some embodiments, a first stem sequence can be at least 5, at least 10, at least 15, at least 20, at least 25, at least 30, at least 35, at least 40, at least 45, at least 50, at least 60, at least 70, at least 80, or at least 90 nucleotides long. In some embodiments, a first stem sequence can be at most 125, at most 110, at most 100, at most 90, at most 80, at most 70, at most 60, at most 50, at most 40, at most 30, at most 20, or at most 15 nucleotides long. In some embodiments, a second stem sequence can be at least 5, at least 10, at least 15, at least 20, at least 25, at least 30, at least 35, at least 40, at least 45, at least 50, at least 60, at least 70, at least 80, or at least 90 nucleotides long. In some embodiments, a second stem sequence can be at most 125, at most 110, at most 100, at most 90, at most 80, at most 70, at most 60, at most 50, at most 40, at most 30, at most 20, or at most 15 nucleotides long.

In some embodiments, a first payload sequence and/or a second payload sequence include an encoding region. In some embodiments, an encoding region encodes a gene product. In some embodiments, a gene product is an RNA or a polypeptide. In some embodiments, an encoding region encodes a fusion polypeptide or a chimeric polypeptide.

In some embodiments, a first payload sequence and/or a second payload sequence include one or more regulatory elements. In some embodiments, one or more regulatory elements are selected from the group consisting of a promoter, a transcriptional activator, an enhancer, a polyadenylation signal, a splice site, an internal ribosome entry site, a viral 2A element, and combinations thereof.

In some embodiments, a first payload sequence and/or a second payload sequence are 50 nucleotides to 25,000 nucleotides in length.

In some embodiments, a first payload oligonucleotide further comprises a first 5' spacer and a first 3' spacer so that the first payload oligonucleotide includes in 5' to 3' order the first 5' extension sequence, the first 5' spacer, the first payload sequence, and the first 3' spacer. In some embodiments, a first 5' spacer and/or a first 3' spacer comprise at least 1 nucleotide, at least 2 nucleotides, at least 3 nucleotides, at least 4 nucleotides at least 5 nucleotides, at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, or at least 60 nucleotides. In some embodiments, a first 5' spacer and/or a first 3' spacer are at most 1,500 nucleotides, at most 1,400 nucleotides, at most 1,300 nucleotides, at most 1,200 nucleotides, at most 1,1100 nucleotides, at most 1,000 nucleotides, at most 900 nucleotides, at most 800 nucleotides, at most 700 nucleotides, at most 500 nucleotides, at most 400 nucleotides, at most 300 nucleotides, at most 250 nucleotides, 200 nucleotides, at most 180 nucleotides, at most 160 nucleotides, at most 150 nucleotides, at most 140 nucleotides, at most 120 nucleotides, at most 110 nucleotides, at most 100 nucleotides, at most 90 nucleotides, or at most 80 nucleotides.

In some embodiments, a second payload oligonucleotide further comprises a second 5' spacer and a second 3' spacer so that the second payload oligonucleotide includes in 5' to 3' order the second 5' extension sequence, the second 5' spacer, the second payload sequence, and the second 3' spacer. In some embodiments, a second 5' spacer and/or a second 3' spacer are at least 5, at least 10, at least 15, at least 20, at least 25, at least 30, at least 35, at least 40, at least 45, or at least 50 nucleotides long nucleotides in length. In some embodiments, a second 5' spacer and/or a second 3' spacer are at least at most 100, at most 90, at most 80, at most 70, at most 60, at most 50, at most 40, at most 30, at most 20, or at most 15 nucleotides long.

In some embodiments, (i) a first payload oligonucleotide further comprises a first 5' spacer and a first 3' spacer so that the first payload oligonucleotide includes in 5' to 3' order the first 5' extension sequence, the first 5' spacer, the first payload sequence, and the first 3' spacer; and (ii) a second payload oligonucleotide further comprises a second 5' spacer and a second 3' spacer so that the second payload oligonucleotide includes in 5' to 3' order the second 5' extension sequence, the second 5' spacer, the second payload sequence, and the second 3' spacer; wherein the first 5' spacer is complementary to the second 3' spacer and/or the first 3' spacer is complementary to the second 5' spacer.

In certain embodiments, provided are compositions comprising a first payload oligonucleotide including a first payload sequence and a first 3' extension sequence; (ii) a second payload oligonucleotide including a second payload sequence and a second 3' extension sequence, wherein the first payload sequence is complementary to the second payload sequence; (iii) a third payload oligonucleotide including the first payload sequence and a first 5' extension sequence; (iv) a fourth payload oligonucleotide including the second payload sequence and a second 5' extension sequence; (v) a first adaptor oligonucleotide comprising: (a) a first stem sequence and a second stem sequence, wherein the first stem sequence is an inverted complement of the second stem sequence, and (b) a first adaptor 3' extension sequence that is complementary to the first 3' extension sequence; (vi) a second adaptor oligonucleotide comprising: (a) a third stem sequence and a fourth stem sequence, wherein the third stem sequence is an inverted complement of the fourth stem sequence, and (b) a second adaptor 3' extension sequence that is complementary to the second 3' extension sequence; (vii) a third adaptor oligonucleotide comprising: (a) a fifth stem sequence and a sixth stem sequence, wherein the fifth stem sequence is an inverted complement of the sixth stem sequence, and (b) a first adaptor 5' extension sequence that is complementary to the first 5' extension sequence; and (viii) a fourth adaptor oligonucleotide comprising: (a) a seventh stem sequence and an eighth stem sequence, wherein the seventh stem sequence is an inverted complement of the eighth stem sequence, and (b) a second adaptor 5' extension sequence that is complementary to the second 5' extension sequence.

In some embodiments, a composition comprises a ligase. In some embodiments, a ligase is a temperature dependent ligase. In some embodiments, a ligase is a thermostable ligase.

In some embodiments, a first stem sequence is identical to a third stem sequence, and a second stem sequence is identical to a fourth stem sequence.

In another aspect, provide are methods of generating 1 cc nucleic acid vectors, e.g., 1 cc DNA vectors.

In certain embodiments, provided are methods of generating a linear covalently closed DNA vector comprising cycling the temperature of a provided composition comprising a ligase through a first temperature and a second temperature, wherein the first temperature is higher than the second temperature.

In some embodiments, the temperature of a composition is cycled through a first temperature, a second temperature, and a third temperature. In some embodiments, the first temperature is higher than the second temperature, and the third temperature is within two degrees Celsius of an optimal temperature for the ligase. In some embodiments, the third temperature is within 0.5 degrees Celsius of an optimal temperature for the ligase.

In some embodiments, the temperature of a composition is cycled for 10-100 cycles.

In some aspects, provide are uses of provided compositions for the generation of a linear covalently closed DNA vector.

In certain embodiments, provided are methods of generating a linear covalently closed DNA vector comprising: (i) performing a first amplification reaction on a first sample, thereby producing first amplification products, the first sample comprising: (a) at least one copy of a first single stranded nucleotide that includes a first payload sequence, (b) at least one copy of a second single stranded nucleotide that includes a second payload sequence, wherein the first payload sequence is complementary to the second payload sequence, (c) a first primer that includes a sequence complementary to a portion of the 5' end of the second payload sequence and a first extension sequence, and (d) a second primer that includes a sequence complementary to a portion of the 5' end of the first payload sequence; (ii) performing a second amplification reaction on a second sample, thereby producing second amplification products, the second sample comprising: (a) at least one copy of the first single stranded nucleotide that includes the first payload sequence, (b) at least one copy of the second single stranded nucleotide that includes a second payload sequence, (c) a third primer that includes a sequence complementary to a portion of the 5' end of the second payload sequence, and (b) a fourth primer that includes a sequence complementary to a portion of the 5' end of the first payload sequence and a second extension sequence; (iii) forming a composition comprising: (a) the first and second amplification products, (b) a set of adaptor oligonucleotides including: (i) a first adaptor oligonucleotide comprising: (a) a first stem sequence and a second stem sequence, wherein the first stem sequence is an inverted complement of the second stem sequence, and (b) a first adaptor 5' extension sequence that is complementary to the first extension sequence, (ii) a second adaptor oligonucleotide comprising: (a) a third stem sequence and a fourth stem sequence, wherein the third stem sequence is an inverted complement of the fourth stem sequence, and (b) a second adaptor 5' extension sequence that is complementary to the second extension sequence, (iii) a third adaptor oligonucleotide comprising: (a) a fifth stem sequence and a sixth stem sequence, wherein the fifth stem sequence is an inverted complement of the sixth stem sequence, and (b) a third adaptor 3' extension sequence that is the same as the first extension sequence, and (iv) a fourth adaptor oligonucleotide comprising: (a) a seventh stem sequence and an eighth stem sequence, wherein the seventh stem sequence is an inverted complement of the eighth stem sequence, and (b) a fourth adaptor 3' extension sequence that is the same as the second extension sequence; and (c) a ligase; and (iv) cycling the temperature of a composition through a first temperature and a second temperature, wherein the first temperature is higher than the second temperature.

In some embodiments, a first and a second primer of a first amplification reaction and a first and a second primer of a second amplification reaction comprise a 5' phosphate.

In some embodiments, methods further comprise contact a first and a second amplification products with a kinase.

In some embodiments, methods further comprise a step of removing primers. In some embodiments, the step of removing primers comprises using a purification column.

In some embodiments, the step of removing primers comprises incubating a first and/or a second amplification product with a exonuclease.

In some embodiments, a first stem sequence is identical to a fifth stem sequence, and a second stem sequence is identical to a sixth stem sequence. In some embodiments, a third stem sequence is identical to a seventh stem sequence, and a fourth stem sequence is identical to an eighth stem sequence.

In some aspects, provided are linear covalently closed DNA vectors. In some embodiments, a linear covalently closed DNA vector includes: a single strand of DNA that includes: a first payload sequence; a second payload sequence hybridized to the first payload sequence; a first end region comprising a first stem sequence and a second stem sequence, wherein the first stem sequence is hybridized to the second stem sequence so that the first end region forms a hairpin, and wherein the 5' end of the first end region is covalently bound to the 3' end of the first payload sequence and the 3' end of the first end region is covalently bound to the 5' end of the second payload sequence; and a second end region comprising a third stem sequence and a fourth stem sequence, wherein the third stem sequence is hybridized to the fourth stem sequence so that the second end region forms a hairpin, and wherein the 5' end of the second end region is covalently bound to the 3' end of the second payload sequence and the 3' end of the second end region is covalently bound to the 5' end of the first payload sequence, wherein each of the first and the second end regions comprises an end of the linear covalently closed DNA vector, and wherein there are at least 30 nucleotides between each end and the closest 5' nucleotide of the first or second payload sequences to the respective end.

In some embodiments, there are at least 40, 45, 50, 55, 60, 65, 70, 75, 80, 85, 90, 95, 100, 105, 110, 115, or 120 nucleotides between each end and the closest 5' nucleotide of a first or a second payload sequence to the respective end.

In some embodiments, a first payload sequence includes an encoding region between a gene regulatory element and a transcription terminator, the first end region includes an end proximal to the gene regulatory element and the second end region includes an end proximal to the transcription terminator, there are at least 30 nucleotides between the gene regulatory element and the end proximal to the gene regulatory element, and there are at least 30 nucleotides between the transcription terminator and the end proximal to the transcription terminator.

In some embodiments, there are at least 40, 45, 50, 55, 60, 65, 70, 75, 80, 85, 90, 95, 100, 105, 110, 115, or 120 nucleotides between a gene regulatory element and an end proximal to the gene regulatory element, and wherein there are at least 40, 45, 50, 55, 60, 65, 70, 75, 80, 85, 90, 95, 100, 105, 110, 115, or 120 nucleotides between a transcription terminator and an end proximal to the transcription terminator.

In some embodiments, a first and/or a second end region comprises one or more chemical modifications. In some embodiments, a chemical modification comprises a modified nucleotide base.

In some embodiments, a first and/or a second end region comprises a label.

In some embodiments, a first and/or a second end region is associated with a cell-penetrating peptide.

In some embodiments, a first and/or a second end region is associated with a polyamide.

In some embodiments, a first and/or a second end region is associated with an antigen-specific targeting ligand.

In some embodiments, a first and/or a second end region is associated with a nuclear localization sequence peptide.

In some embodiments, a first and/or a second end region is fully double-stranded.

In some embodiments, a first and/or a second end region comprises a double-stranded portion and a single-stranded loop portion, wherein each single-stranded loop portion comprises an end of the linear covalently closed DNA vector.

BRIEF DESCRIPTION OF THE DRAWING

The Drawing included herein, which is comprised of the following Figures, is for illustration purposes only and not for limitation.

CERTAIN DEFINITIONS

Figure 1:
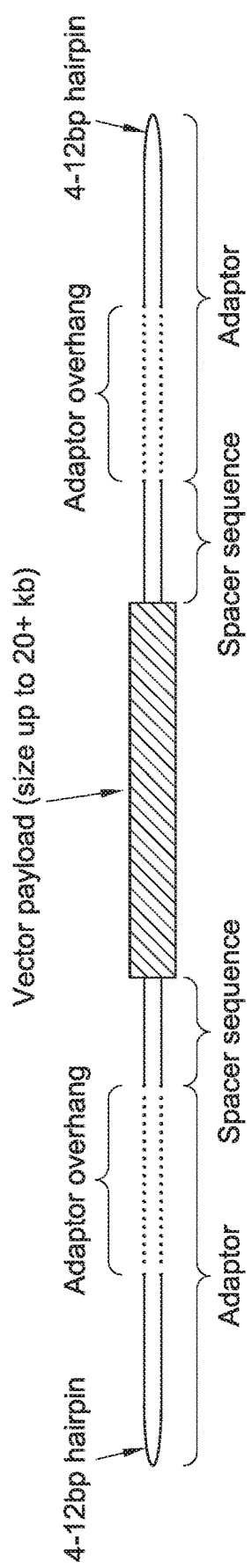
FIG. 1 depicts an example of a linear covalently closed (1 cc) DNA vector. Sizes of various elements are provided by way of example and are not intended to be limiting.

About or approximately: As used herein, the terms "about" and "approximately," when used herein in reference to a value, refers to a value that is similar, in context to the referenced value. In general, those skilled in the art, familiar with the context, will appreciate the relevant degree of variance encompassed by "about" or "approximately" in that context. For example, in some embodiments, the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Amplification: As used herein, the term "amplification," when used in reference to polynucleotides, refers to a method that increases the representation in a population of a specific nucleotide sequence (e.g., from a template polynucleotide) in a sample by producing multiple (i.e., at least 2) copies of the desired nucleotide sequence. Methods for nucleic acid amplification are known in the art and include, but are not limited to, polymerase chain reaction (PCR) and ligase chain reaction (LCR) (i.e., a reaction using both a DNA polymerase and a DNA ligase, as well as two probes that are ligated together to form a single probe during LCR). Variants of standard PCR or LCR reactions can also be used. A "copy" or "amplicon" does not necessarily have perfect sequence complementarity or identity to the nucleotide sequence in the template polynucleotide. Unless otherwise specified, one or more copies can comprise one or more mutant copies, i.e., copies containing one or more mutations ("mutant copies") as compared to the nucleotide sequence in the template polynucleotide. Mutant copies can comprise mutations in one or more bases. For example, for template polynucleotides that comprise a coding region with a plurality of codons, mutant copies can comprise mutations in one or more than one codon and within each codon, there can be mutations in one, two, or all three nucleotides of the codon. In general, "mutations" will be understood to include substitutions, insertions or deletions relative to the template polynucleotide.

Complementary: As used herein, the term "complementary" refers to nucleotides or nucleotide sequences that base-pair according to the standard Watson-Crick complementary rules (adenine "A" base pairs with thymine "T", and guanine "G" base pairs with cytosine "C"). Nucleotide sequences that are "100% complementary" or which exhibit "100% complementarity" are nucleotide sequences which base-pair with one another across the entirety of at least one of the two nucleotide sequences. An oligonucleotide can be "100% complementary" to a template polynucleotide that is longer than the oligonucleotide (i.e., the oligonucleotide is "100% complementary" to the template polynucleotide if the entire sequence of the oligonucleotide base-pairs with a portion of the template polynucleotide). However, nucleic acid sequences that are "complementary" need not be 100% complementary. Generally, the term "complementary" with respect to two or more nucleic acid sequences refers to there being sufficient complementarity across the two nucleic acid sequences such that they hybridize in stringent conditions and/or at temperatures used during annealing phases of amplification methods, e.g., PCR or LCR.

Hybridized: As used herein, the term "hybridize" or "hybridization" refers to a process where two strands in a double-stranded polynucleotide, or two portions of single-stranded polynucleotide, anneal to each other under appropriately stringent conditions. The phrase "is capable is hybridizing to" refers to the ability of two nucleotide sequences to hybridize to each other under typical hybridization conditions (e.g., in the context of a typical amplification reaction, "hybridize" would refer to the interaction of two complementary nucleotide sequences during the annealing phase). As understood by one of ordinary skill in the art, nucleotide sequences need not have perfect sequence complementarity to hybridize with one another. Those skilled in the art understand how to estimate and adjust the stringency of hybridization conditions such that sequences having at least a desired level of complementarity will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, et al. 1994, Current Protocols in Molecular Biology. John Wiley & Sons, Secaucus, N.J.

Inverted complement: As used herein, the term "inverted complement," when used in reference to a first nucleic acid sequence, refers to a corresponding nucleic acid sequence on the same strand as the first nucleic acid sequence that, when reversed, forms a complement of the first nucleic acid sequence. The intervening sequence of nucleotides between the first nucleic acid sequence and its inverted complement can be any length including zero and non-zero lengths.

Label: The term "label" as used herein refers to any element, molecule, functional group, compound, fragment or moiety that is detectable. In some embodiments, a label is provided or utilized alone. In some embodiments, a label is provided and/or utilized in association with (e.g., joined to) another agent. Examples of labels include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}CU$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinium esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

Nucleic acid: As used herein, the term "nucleic acid" refers to a polymer of at least three nucleotides. In some embodiments, a nucleic acid comprises DNA. In some embodiments, a nucleic acid comprises RNA. In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3 -methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5 -propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues long.

Nucleotide: As used herein, the term "nucleotide" refers to its art-recognized meaning. When a number of nucleotides is used as an indication of a distance, e.g., between elements on a nucleic acid, a certain number of nucleotides refers to the number of nucleotides on a single strand of the nucleic acid between the elements, regardless of whether the nucleic acid is double-stranded, single-stranded, or partly double-stranded and partly single-stranded. Similarly, when a number of nucleotides is used as an indication of size, e.g., of a nucleic acid element, a certain number of nucleotides refers to the number of nucleotides on a single strand, e.g., of a nucleic acid element.

Oligonucleotide: As used herein, the term "oligonucleotide" refers to a string of nucleotides. Oligonucleotides may be obtained by a number of methods including, for example, chemical synthesis, restriction enzyme digestion or PCR. As will be appreciated by one skilled in the art, the length of an oligonucleotide (i.e., the number of nucleotides) can vary widely, often depending on the intended function or use of the oligonucleotide. Generally, oligonucleotides comprise between about 5 and about 300 nucleotides, for example, between about 15 and about 200 nucleotides, between about 15 and about 100 nucleotides, between about 15 and about 50 nucleotides, and between about 20 and about 40 nucleotides. In some embodiments, oligonucleotides are between about 20 and about 40 nucleotides in length.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" may be used to refer to the multiple polypeptides that are physically associated and function together as the discrete unit. In some embodiments, proteins may include moieties other than amino acids (e.g., may be glycoproteins, proteoglycans, etc.) and/or may be otherwise processed or modified. Those of ordinary skill in the art will appreciate that in some embodiments the term "protein" may refer to a complete polypeptide chain as produced by a cell (e.g., with or without a signal sequence), and/or to a form that is active within a cell (e.g., a truncated or complexed form). In some embodiments where a protein is comprised of multiple polypeptide chains, such chains may be covalently associated with one another, for example by one or more disulfide bonds, or may be associated by other means.

Primer: As used herein, the term "primer" is interchangeable with "oligonucleotide primer" and is used herein to refer to an oligonucleotide that acts as a point of initiation of synthesis of a primer extension product when hybridized to a template polynucleotide, when placed under suitable conditions (e.g., buffer, salt, temperature and pH), in the presence of nucleotides and an agent for nucleic acid polymerization (e.g., a DNA-dependent or RNA-dependent polymerase). The primer is preferably single-stranded for maximum efficiency in amplification, but may alternatively be double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. A typical primer comprises a sequence of about 10 to about 50, e.g., about 20 to about 40 nucleotides that is complementary to a sequence in a template polynucleotide.

DETAILED DESCRIPTION OF CERTAIN EMBODIMENTS

I. Compositions

In certain embodiments, provided are compositions comprising: (i) a first payload oligonucleotide including a first payload sequence and a first 3' extension sequence; (ii) a second payload oligonucleotide including a second payload sequence and a second 3' extension sequence, wherein the first payload sequence is complementary to the second payload sequence; (iii) a first adaptor oligonucleotide comprising: (a) a first stem sequence and a second stem sequence, wherein the first stem sequence is an inverted complement of the second stem sequence, and (b) a first adaptor 3' extension sequence that is complementary to the first 3' extension sequence; and (iv) a second adaptor oligonucleotide comprising: (a) a third stem sequence and a fourth stem sequence, wherein the third stem sequence is an inverted complement of the fourth stem sequence, and (b) a second adaptor 3' extension sequence that is complementary to the second 3' extension sequence.

In certain embodiments, provided are compositions comprising: (i) a first payload oligonucleotide including a first payload sequence and a first 5' extension sequence; (ii) a second payload oligonucleotide including a second payload sequence and a second 5' extension sequence, wherein the first payload sequence is complementary to the second payload sequence; (iii) a first adaptor oligonucleotide comprising: (a) a first stem sequence and a second stem sequence, wherein the first stem sequence is an inverted complement of the second stem sequence, and (b) a first adaptor 5' extension sequence that is complementary to the first 5' extension sequence; and (iv) a second adaptor oligonucleotide comprising: (a) a third stem sequence and a fourth stem sequence, wherein the third stem sequence is an inverted complement of the fourth stem sequence, and (b) a second adaptor 5' extension sequence that is complementary to the second 5' extension sequence.

In certain embodiments, provided are compositions comprising (i) a first payload oligonucleotide including a first payload sequence and a first 3' extension sequence; (ii) a second payload oligonucleotide including a second payload sequence and a second 3' extension sequence, wherein the first payload sequence is complementary to the second payload sequence; (iii) a third payload oligonucleotide including the first payload sequence and a first 5' extension sequence; (iv) a fourth payload oligonucleotide including the second payload sequence and a second 5' extension sequence; (v) a first adaptor oligonucleotide comprising: (a) a first stem sequence and a second stem sequence, wherein the first stem sequence is an inverted complement of the second stem sequence, and (b) a first adaptor 3' extension sequence that is complementary to the first 3' extension sequence; (vi) a second adaptor oligonucleotide comprising: (a) a third stem sequence and a fourth stem sequence, wherein the third stem sequence is an inverted complement of the fourth stem sequence, and (b) a second adaptor 3' extension sequence that is complementary to the second 3' extension sequence; (vii) a third adaptor oligonucleotide comprising: (a) a fifth stem sequence and a sixth stem sequence, wherein the fifth stem sequence is an inverted complement of the sixth stem sequence, and (b) a first adaptor 5' extension sequence that is complementary to the first 5' extension sequence; and (viii) a fourth adaptor oligonucleotide comprising: (a) a seventh stem sequence and an eighth stem sequence, wherein the seventh stem sequence is an inverted complement of the eighth stem sequence, and (b) a second adaptor 5' extension sequence that is complementary to the second 5' extension sequence.

In some embodiments, compositions comprise between about 50 and 250 ng/µL total payload oligonucleotides. In some embodiments, compositions comprise about 100 ng/µL total payload oligonucleotides.

In some embodiments, compositions include a molar excess of at least one adaptor oligonucleotide relative to the payload oligonucleotides. In some embodiments, the molar excess is between 2.5-fold and 100-fold, e.g., 2.5-fold, 5-fold, 10-fold, etc.

In some embodiments, compositions include a molar excess of each of the adaptor oligonucleotides present in the composition relative to the payload oligonucleotides. In some embodiments, the molar excess is between 2.5-fold and 100-fold. In some embodiments, the molar excess is 2.5 fold to 50-fold. In some certain embodiments, the molar excess is 2.5-fold. In some certain embodiments, the molar excess is 5-fold. In some certain embodiments, the molar excess is 10-fold.

In some embodiments, compositions comprising a ligase further include one or more additives. For example, additives to reduce secondary structure formation of single-stranded DNA, e.g., DMSO, betaine, glycerol, ethylene glycol, 1,2-propanediol, or combinations thereof, may be added.

Payload Oligonucleotides

Payload oligonucleotides generally comprise a payload sequence as described herein and an extension sequence at their 5' and/or 3' ends. In some embodiments, payload oligonucleotides further comprise an additional element. For example, in some embodiments, payload oligonucleotides comprise a spacer (as described further herein) between the extension sequence and the payload sequence. For example, in payload oligonucleotides having a 5' extension sequence, the payload oligonucleotide can comprise, in 5' to 3' order: an extension sequence, a spacer, and a payload sequence. For example, in payload oligonucleotides having a 3' extension sequence, the payload oligonucleotide can comprise, in 5' to 3' order: a payload sequence, a spacer, and an extension sequence.

As discussed further herein, payload oligonucleotides may be included in compositions use to generate 1 cc nucleic acid vectors. In such vectors in which the payload oligonucleotide comprises a spacer, a possible arrangement of some elements within the 1 cc nucleic acid vector that is generated is shown in FIG. 1. Spacers ("spacer sequences") may be located, for example, between a payload sequence ("Vector payload" in FIG. 1) and sequences extension sequences (which are the sequences complementary to the "adaptor overhang" indicated in FIG. 1).

Payload Sequences

Payload sequences are generally any sequence of interest that are desired to be introduced into a cell, organ, organism, and/or system comprising cells.

In some embodiments, the payload sequence comprises one or more of: an encoding region, a gene regulatory element, and a transcription terminator. Non-limiting examples of gene regulatory elements include promoters, transcriptional activators, enhancers, and polyadenylation signals. In some embodiments, the payload sequence comprises an encoding region, a gene regulatory element, and a transcription terminator, positioned relative to each other such that the encoding region is between the gene regulatory element and the transcription terminator.

In some embodiments, the encoding region encodes a gene product. In some embodiments, the gene product is an RNA. In some embodiments, the encoding region encodes a polypeptide (such as a protein, such as a glycoprotein). In some embodiments, the encoding region encodes a fusion polypeptide and/or a chimeric polypeptide. In some embodiments, the encoding region encodes one gene product. In some embodiments, the encoding region encodes more than one gene product.

In some embodiments, the payload sequence comprises one or more aptamer- or polypeptide-binding domains (e.g., transcription factor binding domains).

In some embodiments, the payload sequence comprises a synthetic nucleic acid.

In some embodiments, the payload sequence comprises at least 50 nucleotides, at least 75 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, at least 500 nucleotides, at least 550 nucleotides, at least 600 nucleotides, at least 650 nucleotides, at least 700 nucleotides, at least 750 nucleotides, at least 800 nucleotides, at least 850 nucleotides, at least 900 nucleotides, at least 950 nucleotides, at least 1000 nucleotides, at least 1100 nucleotides, at least 1200 nucleotides, at least 1300 nucleotides, at least 1400 nucleotides, at least 1500 nucleotides, at least 1600 nucleotides, at least 1700 nucleotides, at least 1800 nucleotides, at least 2000 nucleotides, at least 2500 nucleotides, at least 3000 nucleotides, at least 3000 nucleotides, at least 4000 nucleotides, at least 5000 nucleotides, at least 6000 nucleotides, at least 7000 nucleotides, at least 8000 nucleotides, at least 9000 nucleotides, at least 10,000 nucleotides, at least 11,000 nucleotides, at least 12,000 nucleotides, at least 13,000 nucleotides, at least 14,000 nucleotides, at least 15,000 nucleotides, at least 16,000 nucleotides, at least 17,000 nucleotides, at least 18,000 nucleotides, at least 19,000 nucleotides, at least 20,000 nucleotides, at least 21,000 nucleotides, at least 22,000 nucleotides, at least 23,000 nucleotides, at least 24,000 nucleotides, or at least 25,000 nucleotides.

In some embodiments, the payload sequence is between 50 and 25,000 nucleotides in length, between 100 and 20,000 nucleotides in length, between 500 and 10,000 nucleotides in length, between 1,000 and 8,000 nucleotides in length, and/or between 2,000 and 5,000 nucleotides in length.

Extension Sequences

Extension sequences within payload oligonucleotides can be present at the 5', at the 3' end, or both.

In some embodiments, the extension sequence comprises at least 5 nucleotides, at least 10 nucleotides, at least 15 nucleotides, at least 20 nucleotides, at least 25 nucleotide, at least 30 nucleotides, or at least 35 nucleotides. In some embodiments, the extension sequence comprises at most 50 nucleotides, at most 45 nucleotides, or at most 40 nucleotides. In some embodiments, the extension sequence consists of between 10 and 40 nucleotides, between 15 and 35 nucleotides, and/or between 20 and 25 nucleotides.

Spacers

As used herein, "spacers" refer to nucleic acid sequences that generally do not include any functional elements and do not include any elements that are intended to bind to other molecules (e.g., polypeptides, aptamers, etc.), except that a spacer can hybridize to a complementary spacer (e.g., a spacer on another strand of nucleic acid having a complementary sequence or a spacer that is an inverted complement on the same strand of nucleic acid). Spacers provide distance between one or more elements or between an element and an end.

In some embodiments, a spacer is located between the payload sequence and the first nucleotide of the extension portion. In some embodiments, spacers provide some distance between the payload sequence and the end of the payload oligonucleotide (i.e., such that the spacer, not the payload sequence, is at one end of the payload oligonucleotide).

In some embodiments, payload oligonucleotides comprise two spacers, one spacer between the payload sequence and the extension portion, and one spacer between the payload sequence and one end of the payload oligonucleotide.

In payload oligonucleotides comprising two spacers, the sequences of the spacers can be identical or they can be different.

Sizes of spacers may vary depending on the embodiment. In some embodiments, the spacer comprises at least 1 nucleotide, at least 2 nucleotides, at least 3 nucleotides, at least 4 nucleotides at least 5 nucleotides, at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, or at least 60 nucleotides. In some embodiments, the spacer comprises at most 1,500 nucleotides, at most 1,400 nucleotides, at most 1,300 nucleotides, at most 1,200 nucleotides, at most 1,1100 nucleotides, at most 1,000 nucleotides, at most 900 nucleotides, at most 800 nucleotides, at most 700 nucleotides, at most 500 nucleotides, at most 400 nucleotides, at most 300 nucleotides, at most 250 nucleotides, 200 nucleotides, at most 180 nucleotides, at most 160 nucleotides, at most 150 nucleotides, at most 140 nucleotides, at most 120 nucleotides, at most 110 nucleotides, at most 100 nucleotides, at most 90 nucleotides, or at most 80 nucleotides.

In some embodiments, the spacer consists of between 1 and 1,000 nucleotides. In some embodiments, the spacer consists of between 5 and 500 nucleotides.

Primers

Primers, e.g., primers for use in nucleic acid amplification methods, are generally oligonucleotides that include a sequence complementary to a portion of a payload sequence (e.g., a portion of the 5' end of a payload sequence). Primers can consist of a sequence complementary to a portion of a payload sequence or they can also comprise additional sequences. For an example, a primer can also include an "extension sequence" that is not complementary to a portion of a payload sequence. In primers containing such extension sequences, the extension sequences are generally at the 5' end of the primer, and the portions that are complementary to a portion of a payload sequence are generally at the 3' end of the primer.

In some embodiments, the extension portion comprises at least 5 nucleotides, at least 10 nucleotides, at least 15 nucleotides, or at least 20 nucleotides. In some embodiments, the extension portion comprises at most 50 nucleotides, at most 45 nucleotides, or at most 40 nucleotides. In some embodiments, the extension portion consists of between 10 and 40 nucleotides, between 15 and 35 nucleotides, and/or between 20 and 25 nucleotides.

In some embodiments, one or more primers comprise a 5' phosphate group.

Adaptor Oligonucleotides

Adaptor oligonucleotides generally comprise a hairpin portion and an extension portion.

Adaptor oligonucleotides can be of any size. For example, in some embodiments, adaptor oligonucleotides comprise at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, or at least 100 nucleotides. In some embodiments, adaptor oligonucleotides comprise at most 500 nucleotides, at most 450 nucleotides, at most 400 nucleotides, at most 350 nucleotides, at most 300 nucleotides, at most 250 nucleotides, at most 200 nucleotides, or at most 150 nucleotides. In some embodiments, adaptor oligonucleotides consist of between 90 and 300 nucleotides, between 100 and 300 nucleotides, between 100 and 200 nucleotides, between 200 and 300 nucleotides, or between 150 and 300 nucleotides. In some embodiments, adaptor oligonucleotides consist of between 50 and 150 nucleotides, between 80 and 120 nucleotides, between 90 and 110 nucleotides, and/or between 95 and 105 nucleotides.

In some embodiments, adaptor oligonucleotides do not contain any functional elements.

In some embodiments, adaptor oligonucleotides comprise one or more functional elements. For example, functional elements such as gene regulatory elements (e.g., promoters and/or enhancers, including phage gene regulatory elements), transcriptional terminators, viral elements (e.g., long terminal repeat elements), transposon elements (e.g., terminal inverted repeat elements), selectable markers (e.g., antibiotic resistance genes), origins of replication, replication initiation genes (e.g., repA, such as N15 repA), nucleic acid aptamers, or any combination thereof can be included.

In some embodiments, adaptor oligonucleotides comprise one or more recognition sites, recombinase recognition sites (e.g., loxP sites, frt sites, attP sites, attB sites, etc.), restriction enzyme recognitions sites, etc.

The extension portion can be at the 5' end or the 3' end of the adaptor oligonucleotide and generally is not complementary to any other portion of the adaptor oligonucleotide. In some embodiments, the extension portion comprises at least 5 nucleotides, at least 10 nucleotides, at least 15 nucleotides, or at least 20 nucleotides. In some embodiments, the extension portion comprises at most 50 nucleotides, at most 45 nucleotides, or at most 40 nucleotides. In some embodiments, the extension portion consists of between 10 and 40 nucleotides, between 15 and 35 nucleotides, and/or between 20 and 25 nucleotides.

In some embodiments, an extension portion of an adaptor oligonucleotide is complementary to an extension portion of another molecule described herein, e.g., extension portion of a payload oligonucleotide and/or of a primer. For example, an extension sequence at the 3' end of an adaptor oligonucleotide (a "3' extension sequence") can be complementary to an extension sequence at the 3' end of a payload oligonucleotide and/or at the 5' end of a primer. As a further example, an extension sequence at the 5' end of an adaptor oligonucleotide (a "5' extension sequence") can be complementary to an extension sequence at the 5' end of a payload oligonucleotide and/or at the 5' end of a primer.

In some embodiments, an extension portion of an adaptor oligonucleotides is identical, or comprises a portion that is identical, to an extension portion of another molecule described herein, e.g., extension portion of a payload oligonucleotide and/or of a primer. For example, an extension sequence at the 3' end of an adaptor oligonucleotide (a "3' extension sequence") can be identical to (or comprise a portion that is identical to) an extension sequence at the 5' end of a primer. As a further example, an extension sequence at the 5' end of an adaptor oligonucleotide (a "5' extension sequence") can be identical to (or comprise a portion identical to) an extension sequence at the 5' end of a primer.

Hairpin portions generally comprise a first and a second stem sequence that are inverted complements of each other. In some embodiments, hairpin portions consist of the first and second stem sequences, and the first and second stem sequences are adjacent to one another (i.e., with no intervening nucleotides). In some embodiments, hairpin portions comprise a loop sequence between the first and second stem sequence. The loop sequence is generally not complementary to either the first or second stem sequence. In some embodiments, the loop sequence is not complementary to any portion of the extension sequence.

Under certain conditions suitable for hybridization of nucleic acids, the first and stem sequences hybridize with one another, such that adaptor oligonucleotides of the present disclosure can adopt one of several structures, including (1) a hairpin with no single-stranded loop, and an extension sequence, and/or (2) a hairpin with a single-stranded loop, and an extension sequence.

In some embodiments, each stem sequence has a minimum GC (guanine-cytosine) content of at least 30%, e.g., at least 35%, at least 40%, at least 45%, at least 50%, at least 55%, at least 60%, or at least 65%. In some embodiments, each stem sequence has a maximum GC content of at most 80%, at most 75%, at most 70%, at most 65%, at most 60%, or at most 55%. In some embodiments, each stem sequence has a GC (guanine-cytosine) content of between 45 and 55%.

In some embodiments in which the hairpin portion comprises a loop sequence, the loop sequence comprises at least one nucleotide, at least 2 nucleotides, at least 3 nucleotides, at least 4 nucleotides, at least 5 nucleotides, or at least 6 nucleotides. In some embodiments in which the hairpin portion comprises a loop sequence, the loop sequence comprises at most 15 nucleotides, at most 14 nucleotides, at most 13 nucleotides, at most 12 nucleotides, at most 11 nucleotides, at most 10 nucleotides, or at most 9 nucleotides. In some embodiments, the loop sequence consists of between 5 and 10 nucleotides and/or between 6 and 9 nucleotides.

In some embodiments, all nucleotides within a given adaptor oligonucleotide are naturally occurring nucleotides having one of the four standard bases for DNA (adenine, guanine, cytosine, thymine) or for RNA (adenine, cytosine, and guanine, and uracil).

In some embodiments, adaptor oligonucleotides comprise one or more chemical modifications.

In some embodiments, the chemical modification consists of or comprises a phosphate group at the 5' end of the adaptor oligonucleotide.

In some embodiments, the chemical modification is a modified nucleotide. For example, suitable modifications include, but are not limited to, azides, hexynyl, biotin-azide conjugates, dibenylcyclooctyne, etc. In some embodiments, a modification of one or more nucleotides is introduced by click chemistry, e.g., using NHS ester functional groups.

In some embodiments, adaptor oligonucleotides comprise a label as described further herein.

In some embodiments, adaptor oligonucleotides are associated with one or more moieties. The association can be covalent or non-covalent. Non-limiting examples of moieties include cell-penetrating peptide (e.g., penetratin, Tat peptide, pVEC, transportan, MPG family members, hCT (human calcitonin) and hCT-derived family members, Pep-1, MAP (model amphipathic peptide), $R_6W_3$ peptide), polyamides, antigen-specific targeting ligands, nuclear localization sequences, and DNA nuclear targeting sequences.

In some embodiments, adaptor oligonucleotides are purified (e.g., via a column such as HPLC) before inclusion in provided compositions and/or use in provided methods.

Ligases

In some embodiments, provided compositions comprise one or more ligases. In some embodiments, the ligase is temperature-sensitive. In some embodiments, the ligase is thermostable. Non-limiting examples of suitable ligases include Taq ligase (e.g., Taq ligase from *Thermus thermophilus*, HiFi Ligase (New England Biolabs), etc.), Ampligase (Epicentre), 9° N ligase (New England Biolabs), Tsc ligase (from *Thermus scotoductus*), Tth (from *Thermus thermophilus*) ligase, Rma ligase (from *Rhodothermus marinus*), Tfi ligase (from *Thermus filiformis*), and Bst ligase (from *Bacillus stearothermophilus*).

II. Vectors

In one aspect of the present disclosure, provided are linear covalently closed (1 cc ) nucleic acid vectors. In some embodiments, 1 cc vectors are DNA vectors. In some embodiments, 1 cc vectors are RNA vectors.

In some embodiments, provided 1 cc vectors are a single strand of a nucleic acid including a first payload sequence (as described herein), a second payload sequence (as described herein) hybridized to the first payload sequence, and first and second end regions as described herein, with the 5' end of the first end region being covalently bound to the 3' end of the first payload sequence, the 3' end of the first end region being covalently bound to the 5' end of the second payload sequence, the 5' end of the second end sequence being covalently bound to the 3' end of the second payload sequence, and the 3' end of the second end sequence being covalently bound to the 5' end of the first payload sequence.

In some embodiments, there are at least 30 nucleotides between each end (as described herein) of the 1 cc vector and the closest 5' nucleotide of the first or second payload sequences to the respective end. In some embodiments, there are at least 40, 45, 50, 55, 60, 65, 70, 75, 80, 85, 90, 95, 100, 105, 110, 115, or 120 nucleotides between each end and the closest 5' nucleotide of the first or second payload sequences to the respective end.

In some embodiments in which the payload sequence comprises an encoding region, a gene regulatory element, and a transcription terminator, positioned relative to each other such that the encoding region is between the gene regulatory element and the transcription terminator (as mentioned herein), there are at least 30 nucleotides between the gene regulatory element and the end proximal to the gene regulatory element, and there are at least 30 nucleotides between the transcription terminator and the end proximal to the transcription terminator. In some embodiments, there are at least 40, 45, 50, 55, 60, 65, 70, 75, 80, 85, 90, 95, 100, 105, 110, 115, or 120 nucleotides between the gene regulatory element and the end proximal to the gene regulatory element. In some embodiments, there are at least 40, 45, 50, 55, 60, 65, 70, 75, 80, 85, 90, 95, 100, 105, 110, 115, or 120 nucleotides between the transcription terminator and the end proximal to the transcription terminator.

End Regions

End regions generally comprise a first stem sequence and a second stem sequence hybridized to the first stem sequence. The first stem sequence and second stem sequences are generally on the same strand of nucleic acid and are inverted complements of each other. In some embodiments, an end region consists of the first stem sequence and the second stem sequence, with no nucleotides intervening between them. In some embodiments, an end region comprises, in addition to the first stem sequence and the second stem sequence, a loop sequence positioned between the first and second stem sequences. Sizes and/or GC content of stem sequences and loop sequences can be as described for stem sequences and loop sequences in the "adaptor oligonucleotides" section herein.

Under certain conditions suitable for hybridization of nucleic acids, the first and stem sequences hybridize with one another, such that within each 1 cc , each end region comprises a (1) a hairpin with no single-stranded loop (e.g., a fully double-stranded hairpin) or (2) a hairpin with a double-stranded stem region and single-stranded loop.

Each end region comprises an end of the 1 cc vector. For end regions comprising a hairpin with no single-stranded loop, the end is the pair of nucleotides, one of which is in the first stem sequence, the other of which is in the second stem sequence, which are adjacent to each other on the same strand of the nucleic acid. This pair of nucleotides can not only form hydrogen bonds with each other (e.g., with Watson-Crick base-pairing), but are also covalently linked by virtue of being adjacent to one another on the same strand of nucleic acid. For end regions comprising a hairpin with a single-stranded loop, the end is either the nucleotide at the midpoint of the loop (for loops consisting of an odd number of nucleotides) or the pair of nucleotides adjacent to each other within the loop and flanking the mid-point of the loop (for loops consisting of an even number of nucleotides).

In some embodiments, an end region comprises one or more chemical modifications (e.g., a modified nucleotide base). In some embodiments, an end region is labeled. In some embodiments, an end region is associated (either covalently or non-covalently) with a moiety such as any of the moieties mentioned herein in the context of association with adaptor oligonucleotides.

Delivery

Provided vectors can be delivered to cells by any of a variety of known methods in the art, including, but not limited to, transfection into cells (e.g., via electroporation, chemical methods, etc.), delivery via particles (e.g., nanoparticles), and/or administration to an organism (e.g., by any suitable administration route). Cells to which vectors can be delivered can be, for example, cultured cells, and/or cells within a tissue and/or an organism.

III. Methods

In some embodiments, provided are methods of generating a linear covalently closed nucleic acid vector, e.g., a DNA vector, comprising cycling the temperature of a provided composition comprising a ligase (as described herein) through a first temperature and a second temperature, wherein the first temperature is higher than the second temperature.

In some embodiments, the temperature of the composition is cycled through the first temperature, the second temperature, and a third temperature, wherein the third temperature is within two degrees Celsius of an optimal temperature for the ligase. In some embodiments, wherein the third temperature is within 0.5 degrees Celsius of an optimal temperature for the ligase.

In some embodiments, the first temperature is between about 90 and about 98° C., e.g., about 94° C. or 95° C. In some embodiments, the duration during which the composition is kept at the first temperature is between about 10 seconds and 2 minutes during each cycle.

In some embodiments, the second or the third temperature is between about 40 and about 70° C., e.g., about 60° C. or about 65° C. In some embodiments, the duration during which the composition is kept at the second or third temperature is between about 2.5 minutes and about 30 minutes during each cycle In some embodiments, the temperature of the composition is cycled for 10 to 100 cycles, e.g., 25-30 cycles, e.g., 30 cycles.

In some embodiments, in lieu of holding the composition at a constant second temperature during each cycle, the composition is cycled through the first temperature, the composition is ramped from an initial second temperature to a final second temperature at a particular rate, e.g., from 40° C. to 70° C. at 0.1° C./sec or from 70° C. to 40° C. to 0.1° C./sec, and optionally held at the final second temperature for a period of time during each cycle.

Figure 2:
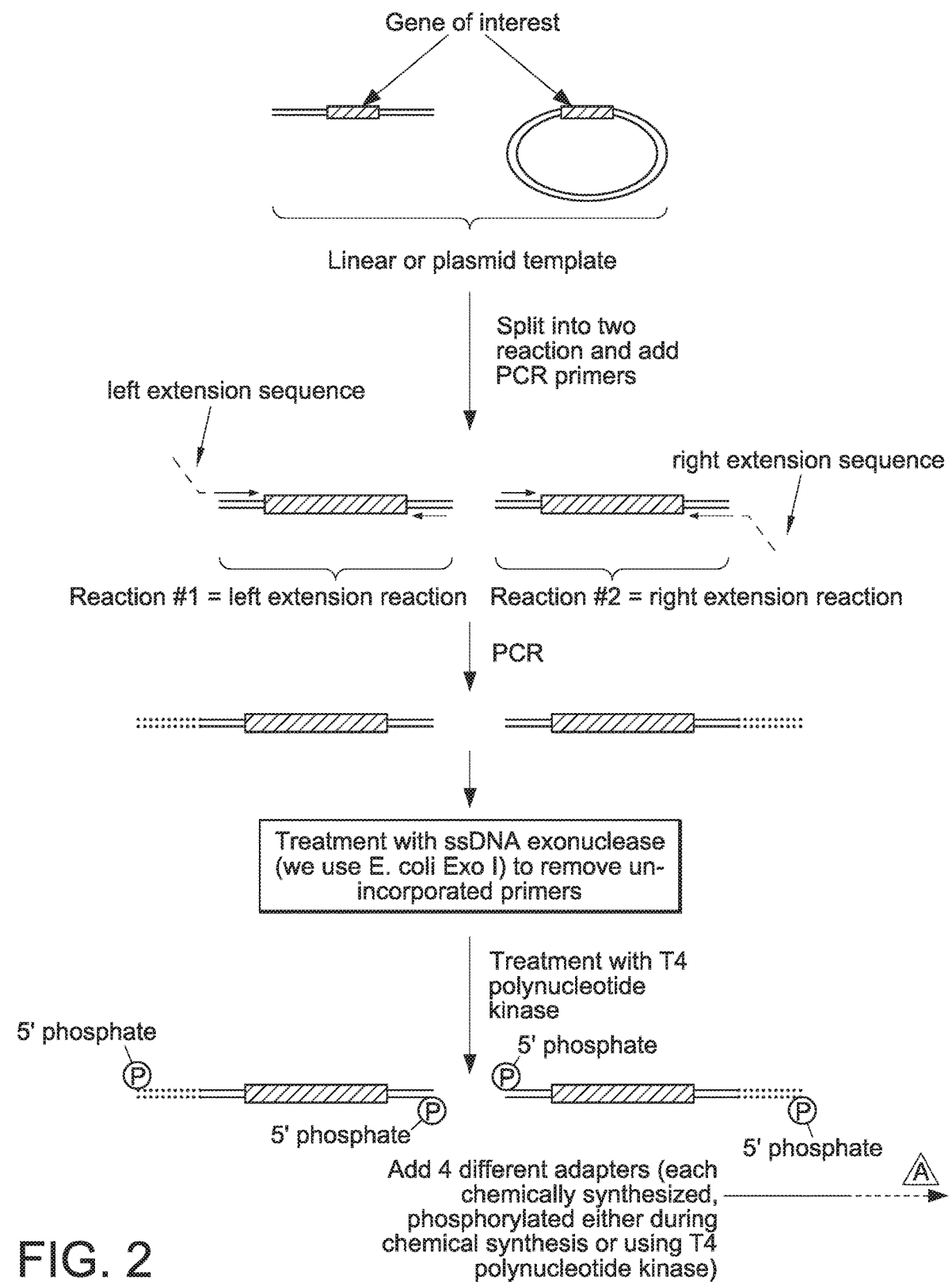
FIG. 2 provides a schematic of a procedure that can be used to generate linear covalently closed DNA vectors in accordance with the present disclosure.

In some embodiments, a provided method of generating a linear covalently closed nucleic acid vector includes steps as depicted in FIG. 2. FIG. 2 provides a schematic of a procedure using disclosed compositions and methods to generate linear covalently closed (1 cc) DNA vectors, which includes amplification (on the left side of FIG. 2) and cycling a composition including a ligase through at least two temperatures (melting and annealing/ligating) (on the right side of FIG. 2).

On the left side of FIG. 2 is a scheme for a pair of amplification reactions using a common template. Each of the pair of amplification reactions includes one primer without an extension portion (a "short primer") and one primer with an extension portion (a "long primer") relative to a sequence in the intended template. (Extension portions are depicted with dotted lines.) Amplification products (which then comprise either a "left" or a "right" extension sequence) can be treated with a kinase (e.g., PNK) such that both strands of the amplification products are phosphorylated at their 5' ends.

On the right side of FIG. 2 is a schematic for a ligase cycling reaction using products from a pair of amplification reactions such as those illustrated on the left side of FIG. 2. Four adaptor oligonucleotides are included in the ligase cycling reaction, each adaptor oligonucleotide comprising a hairpin portion (depicted with a solid line), an extension portion (depicted with a dotted line), and a 5' phosphate group, with the extension portion designed to hybridize to one of the four possible extension sequences (first or second strand of the left or right extension sequence):

Cycling through melting and annealing and ligating phases results in the production of 1 cc DNA vectors (depicted at the top of the right side of FIG. 2).

Figure 3:
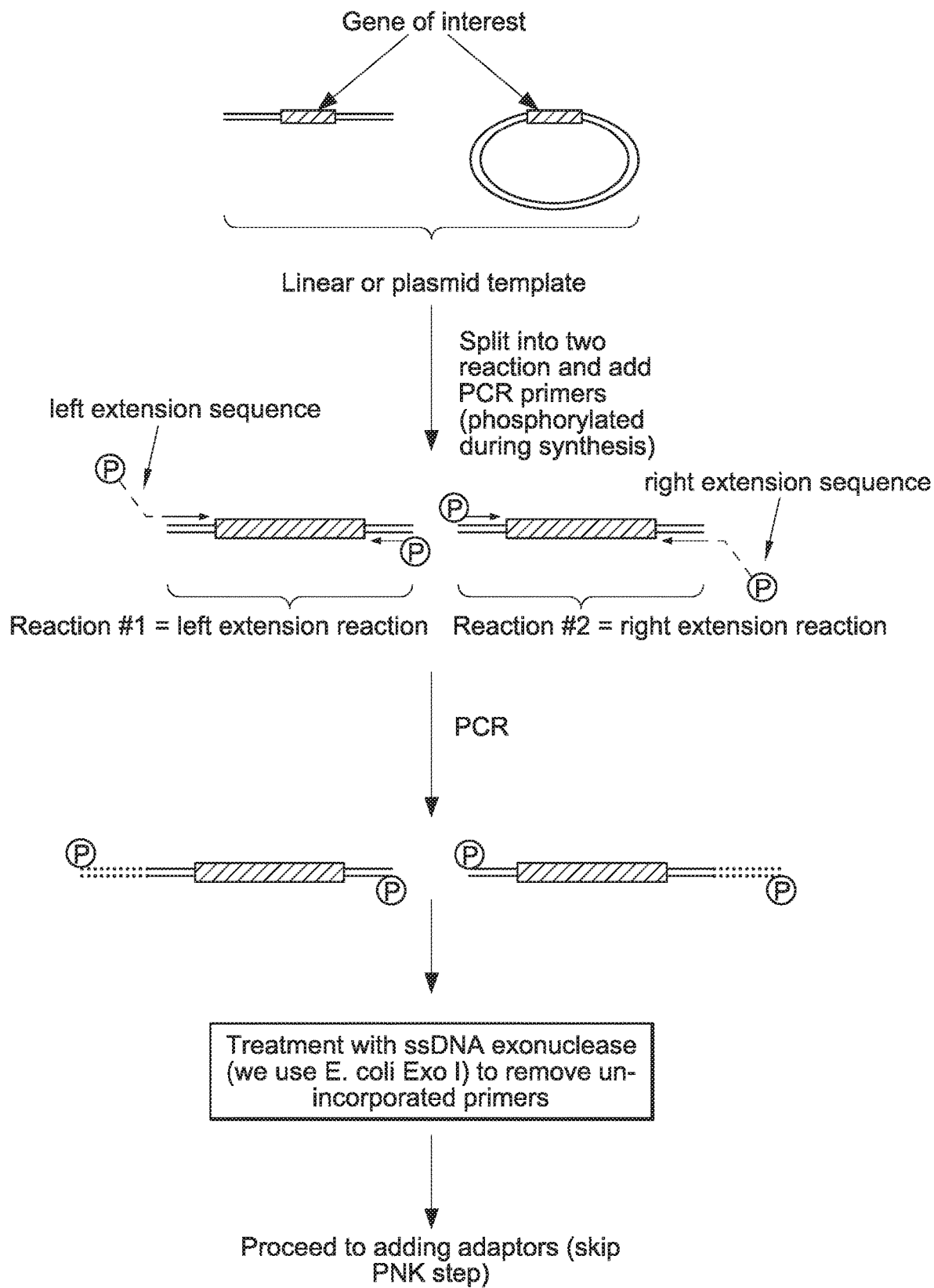
FIG. 3 provides a schematic of a procedure that can be used to generate linear covalently closed DNA vectors in accordance with the present disclosure.

In some embodiments, a provided method of generating a linear covalently closed nucleic acid vector includes steps as depicted in FIG. 3. FIG. 3 depicts another schematic of a procedure using disclosed compositions and methods to generate 1 cc DNA vectors. The schematic outlined in FIG. 2 is followed, except that no step of treating amplification products with a kinase is included. Primers used in each of the pair of amplification reactions comprise 5' phosphate groups, such that both strands of the amplification products are phosphorylated at their 5' ends.

Figure 4:
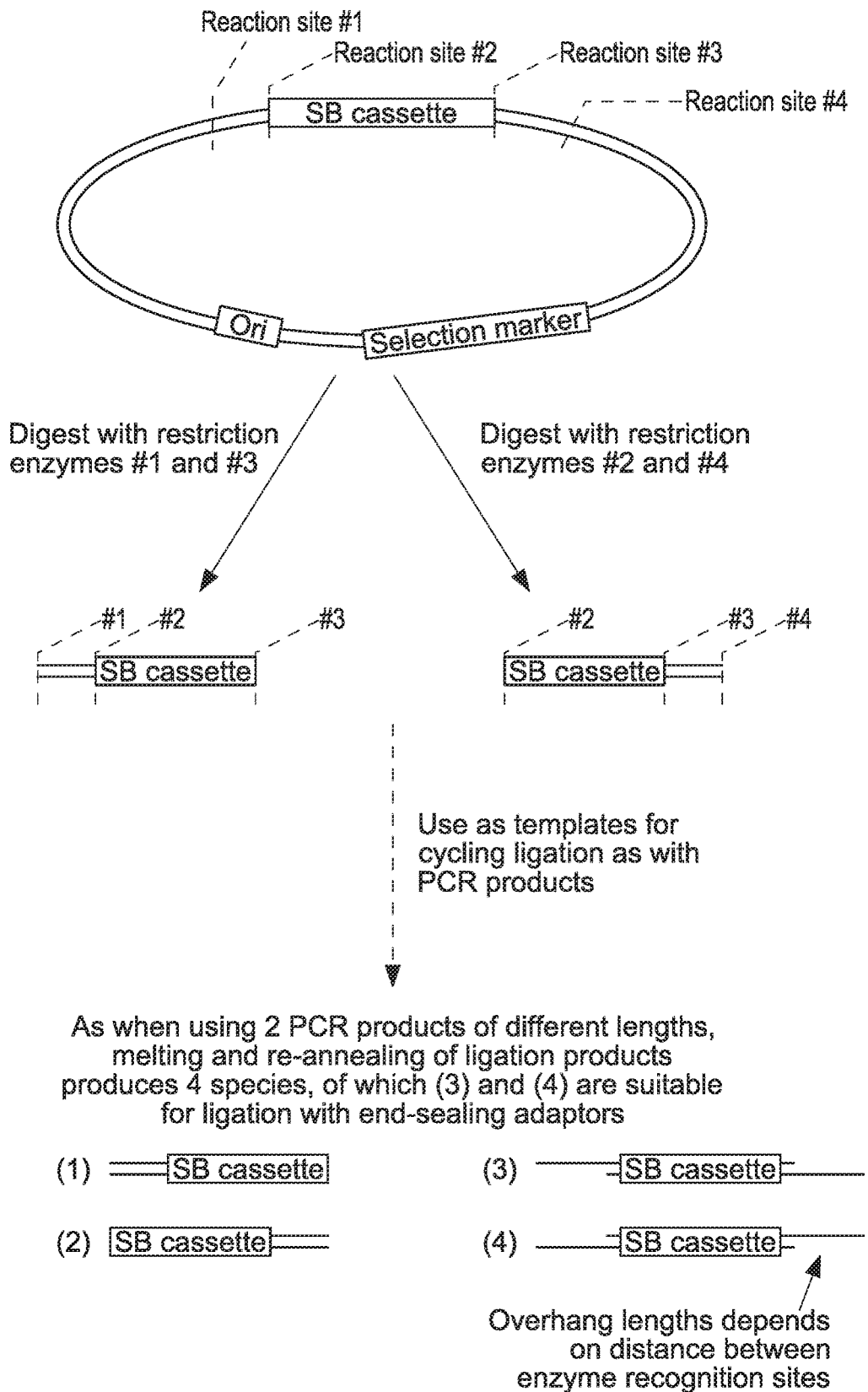
FIG. 4 provides a schematic of a procedure that can be used to generate linear covalently closed DNA vectors in accordance with the present disclosure.

In some embodiments, a provided method of generating a linear covalently closed nucleic acid vector includes steps as depicted in FIG. 4. FIG. 4 describes another schematic of a procedure using disclosed compositions and methods to generate 1 cc DNA vectors. The schematic for a cyclic ligation outlined on the right side of FIG. 2 is followed, but bacterial plasmid production (instead of PCR amplification) is used to provide templates for cyclic ligation to produce 1 cc DNA. In this schematic, templates with long overhangs are produced using restriction endonucleases.

In some embodiments, unwanted components (e.g., primers) present after an amplification reaction are removed before ligase cycling reactions. Any suitable method known in the art for removing such unwanted products can be used. In some embodiments, unwanted components (e.g., primers) can be removed by a method that includes using a purification columns (e.g., affinity purification). In some embodiments, purification columns can use affinity, size exclusion, reverse-phase, magnetic beads, anion exchange, cation exchange, hydrophobic interaction, etc. to separate unwanted components. In some embodiments, a column is a HPLC column. Additionally or alternatively, in some embodiments, unwanted components (e.g., primers) can be removed using a nuclease such as, for example, *E. coli* exonuclease I, RecJF, Exonuclease T, Exonuclease VII, Mung Bean nuclease, etc.

In some embodiments, unwanted components (e.g., unligated and/or incompletely ligated products) are removed after ligase cycling reactions. Any suitable method known in the art for removing such unwanted products can be used. In some embodiments, such unwanted components are removed using an exonuclease, e.g., *E. coli* T7 Exonuclease, Lambda Exonuclease, Exonuclease III, Exonuclease V/RecBCD, Truncated Exonuclease VIII, T5 Exonuclease, and combinations thereof.

In some embodiments, 1 cc vectors are formed with an efficiency of at least 5%, at least 10%, at least 15%, at least 18%, or at least 20%. In some embodiments, efficiency refers to a percentage of products that are resistant to exonucleases, indicative of the vector being fully closed.

Exemplification

Example 1: Design and Production of Amplification Primers and Adaptor Oligonucleotides to Generate 1 cc DNA Vectors to Express a Luciferase Reporter Gene The present Example demonstrates the design and primers and adaptor oligonucleotides suitable for use in disclosed methods of 1 cc DNA vectors.

Short (without extension portion) and long (with extension portion) primers were designed to anneal to a sequence within pCMV-Gluc2 Control Plasmid (New England Biolabs) (the "template"). Amplification primers for this example were designed to have template-binding sequences with an annealing temperature of 60° C., a 45-55% GC content, and a G or C nucleotide at the 5' end of the primer. However, as is known in the art, the parameters used to select amplification primers can vary based on a number of factors, including the amplification reaction protocol used (e.g., temperatures cycled through, buffer used, etc.) and the target sequence for amplification.

Three different sets of forward primers were synthesized, having the nucleotide sequences shown below. (Sequences are shown the in 5' to 3' direction). Within depicted primer nucleotide sequences, lowercase letters indicate extension portions, and uppercase letter indicate portions complementary to the template.

GLuc_Design-1_fwd_short:
(SEQ ID NO: 1)
CGC TGC TTC GCG ATG TAC GGG

GLuc_Design-1_fwd_long:
(SEQ ID NO: 2)
tgt cgg tta gct cgc tca gct gat gCG CTG CTT CGC GAT GTA CGG G GLuc_Design-2_fwd_short:
(SEQ ID NO: 3)
CTG AGT AGT GCG CGA GCA AAA TTT AAG CTA CAA C GLuc_Design-2_fwd_long:
(SEQ ID NO: 4)
tgt cgg tta gct cgc tca gct gat gCT GAG TAG TGC GCG AGC AAA ATT TAA GCT ACA AC GLuc_Design-3_fwd_short:
(SEQ ID NO: 5)
AGA AGT GGT CCT GCA ACT TTA TCC GCC GLuc_Design-3_fwd_long:
(SEQ ID NO: 6)
tgt cgg tta gct cgc tca gct gat gAG AAG TGG TCC TGC AAC TTT ATC GCC One set of reverse primers was synthesized, having the sequences shown below. (Sequences are shown in 5' to 3' direction.).

GLuc_rev_short:
(SEQ ID NO: 7)
CAG CAC AGA AAA GCA TCT TAC TTG GCA TGA CAG

GLuc_rev_long:
(SEQ ID NO: 8)
ccc tat ggg tcg gcg caa tgc CAG CAC AGA AAA GCA TCT TAC TTG GCA TGA CAG Four different adaptors oligonucleotides were synthesized, each 100 nucleotides long with a hairpin portion and an extension portion. The hairpin portions of each adaptor contained a double-stranded stem having 45-55% GC content and a 9-base loop. The extension portions of each adaptor were complementary to or identical to the extension portions of the primers. Adaptor oligonucleotides were synthesized such that they each contained a 5' phosphate group. Nucleotide sequences of the adaptor oligonucleotides are shown below, with sequences in the 5' to 3' direction. Within depicted adaptor oligonucleotide sequences, lowercase letters indicate extension or hairpin loop portions, and uppercase letter indicate hairpin stem portions.

SB_GLuc_left_5':
(SEQ ID NO: 9)
cat cag ctg agc gag cta acc gac aCT GCG GTC CAA CTC AGG CGT AGA CCT CCt gta tgt tcG GAG GTC TAC GCC TGA GTT GGA CCG CAG SB_GLuc_left_3':
(SEQ ID NO: 10)
CAG CGC GCA ACA GCC TAC CTT CTC GGa cct atc taC CGA GAA GGT AGG CTG TTG CGC GCT Gtg tcg gtt agc tcg ctc agc tga tg SB_GLuc_right_5':
(SEQ ID NO: 11)
gca ttg cgc cga ccc ata ggg CTA ACG AAG GCG CCC GGT ACG GCA tta ccc atc TGC CGT ACC GGG CGC CTT CGT TAG SB_GLuc_right_3':
(SEQ ID NO: 12)
CGT CGG AGT GCG GAT CGA ACC TGG Cta agt agg tGC CAG GTT CGA TCC GCA CTC CGA CGc cct atg ggt cgg cgc aat gc Example 2: Design and Production of Amplification Primers and Adaptor Oligonucleotides to Generate 1 cc DNA Vectors to Express a Luciferase Reporter Gene Amplification primers and adaptor oligonucleotides were synthesized as described in Example 1, except that both the amplification primers and the adaptor oligonucleotides were synthesized with 5' phosphate groups.

Example 3: Production of 1 cc DNA Luciferase Expression Vectors

The present Example demonstrates that compositions and methods of the present disclosure can be used to generate linear covalently closed (1 cc) DNA vectors including a reporter gene.

A luciferase-expressing 1 cc DNA construct was generated as follows.

Three pairs of amplification reactions were performed, each using pCMV-Gluc2 Control Plasmid (New England Biolabs) as the template. Primer pairs used were designed and described in Example 1. The primers used in each pair of amplification reactions are indicated below:

1) SB Design 1
Left extension reaction: GLuc_Design-1_fwd_long & GLuc_rev_short
Right extension reaction: GLuc_Design-1_fwd_short & GLuc_rev_long
2) SB Design 2
Left extension reaction: GLuc_Design-2_fwd_long & GLuc_rev_short
Right extension reaction: GLuc_Design-2_fwd_short & GLuc_rev_long
3) SB Design 3
Left extension reaction: GLuc_Design-2_fwd_long & GLuc_rev_short
Right extension reaction: GLuc_Design-2_fwd_short & GLuc_rev_long Amplification was carried out in 50 µL reactions using Herculase II Fusion DNA polymerase (Agilent Genomics). Each reaction contained 5 ng pCMV-GLuc 2 Control plasmid, 350 nM of each primer, 250 µM of each dNTP, 1× Herculase II buffer, and 1 µL polymerase. Amplification reactions were carried out using the following thermal cycling conditions:

95° C. (2 min)
35 cycles of:
   95° C. (15 sec)
   69° C. (20 sec)
   72° C. (45 sec)
72° C.: (3 min)

Amplification reaction products were purified using a DNA Clean & Concentrator-25 kit (Zymo Research). DNA was eluted using 10 mM Tris-Cl pH 8.5 buffer.

Each amplification product was phosphorylated in a separate reaction containing 200 ng/µL DNA, 1 mM ATP, and 0.5 U/µL T4 Polynucleotide Kinase (New England Biolabs) in 1× T4 PNK Buffer (10 mM $MgCl_2$, 5 mM DTT, 70 mM Tris-Cl pH 7.6). Amplification products were phosphorylated at 37° C. for 16 hr. Following PNK treatment, reactions were diluted with a 1× volume containing 1.2 U/µL Exonuclease I (New England Biolabs) in 2× Exonuclease I buffer (13.4 mM $MgCl2$, 20 mM β-mercaptoethanol, 134 mM glycine-KOH pH 9.5), incubated at 37° C. for 1 hour, and heat-inactivated at 80° C. for 20 minutes. DNA was purified using a DNA Clean & Concentrator-25 kit (Zymo Research), using 10 mM Tris-Cl pH 8.5 as the elution buffer.

Thermal cycling ligation reactions were carried out in 40 µL reactions, each reaction with one of the following pairs of left and right extension products:

1) SB Design 1: 2.5 µg SB Design 1 left extension reaction and 2.5 µg SB Design 1 right extension reaction
2) SB Design 2: 2.5 µg SB Design 2 left extension reaction and 2.5 µg SB Design 2 right extension reaction
3) SB Design 3: 2.5 µg SB Design 3 left extension reaction and 2.5 µg SB Design 3 right extension reaction To each of the above thermal cycling reactions, the four adaptor oligonucleotides described in Example 3 (SB_GLuc_left_5', SB_GLuc_left_3', SB_GLuc_right_5', and SB_GLuc_right_3') were added, each adaptor oligonucleotide at a 5× molar excess with respect to the total template concentration.

Thermal cycling ligation reactions were carried out with 2 U/µL Taq DNA Ligase (New England Biolabs) in 1× Taq DNA Ligase buffer (0.1% Triton X-100, 25 mM potassium acetate, 10 mM magnesium acetate, 10 m DTT, 20 mM Tris-HCl pH 7.6). The following thermal cycling conditions were used:

94° C. (30 seconds)
35 cycles of:
   94° C. (15 seconds)
   70° C. (30 min)
60° C.: (1 hour)

Ligation products were purified using a DNA Clean & Concentrator-25 kit (Zymo Research), using 10 mM Tris-Cl pH 8.5 as the elution buffer.

To remove incompletely ligated fragments and parental plasmid DNA, ligation products were digested in reactions containing 100 ng/µL DNA, 0.1 U/µL DpnI (New England Biolabs), 0.45 U/µL T7 exonuclease (New England Biolabs), and 1× CutSmart Buffer (10 ng/µL bovine serum albumin, 50 mM potassium acetate, 10 mM magnesium acetate, 20 mM Tris-acetate pH 7.9). Digests were carried out at 25° C. for 30 minutes and 37° C. for 30 minutes. DNA was purified using a DNA Clean & Concentrator-25 kit (Zymo Research), using 10 mM Tris-Cl pH 8.5 as the elution buffer.

Figure 5A:
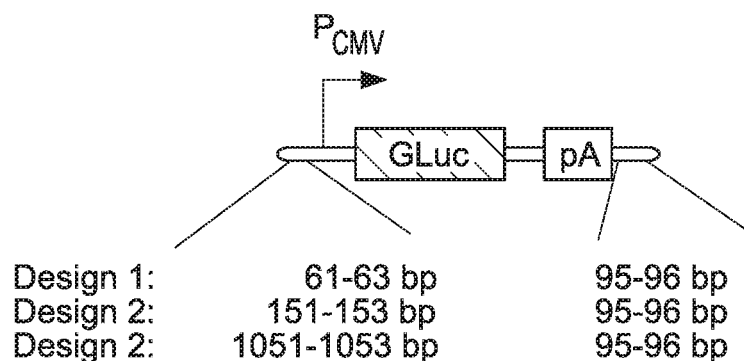
FIG. 5A shows a schematic of three 1 cc DNA luciferase-expression vector designs tested. The designs varied in the spacing between the indicated regulatory regions and the nt. terminal loops. Distances are given as a range due to the small differences in size between the two adaptors used to end-seal each side

FIG. 5A depicts a schematic showing the designs of the three luciferase-expressing 1 cc DNA vectors produced. The total sizes of the three vectors ranged from 1.4 kb to 2.5 kb.

Concentrations of products were determined using agarose gel quantification. Yields of about 20 ng of fully sealed vectors per µL of reaction volume were obtained.

These results indicate that presently disclosed compositions and methods can be used produce robust yields of 1 cc nucleic acid vectors.

Example 4: Cellular Delivery and Expression of 1 cc DNA Luciferase Expression Vectors The present Example demonstrates that 1 cc DNA vectors including a reporter gene provided by aspects of the disclosure can be successfully delivered to and expressed in cells.

NIH3T3/GFP fibroblasts (Cell Biolabs) were cultured in high glucose DMEM (11960 Thermo Fisher Scientific) supplemented with 10% newborn calf serum, 292 µg/mL L-glutamine, 100 U/mL penicillin, and 100 µg/mL streptomycin. Cells were grown on Costar tissue culture-treated vessels (Corning), with passaging performed using TrypLE Express (Thermo Fisher Scientific).

NIH3T3/GFP cells were transfected with 100 ng of either pCMV-GLuc 2 Control Plasmid (New England Biolabs) or one of the 1 cc DNA vectors encoding a luciferase gene generated as described in Example 3 and shown in FIG. 5A. Transfection was performed using Lipofectamine LTX (Thermo Fisher Scientific) using a 5:1 Lipofectamine:DNA ratio and a 1:1 PLUS Reagent:DNA ratio. Two days after transfection, media was collected and assayed for luciferase expression using the BioLux Gaussia Luciferase Assay Kit (New England Biolabs.)

Figure 5B:
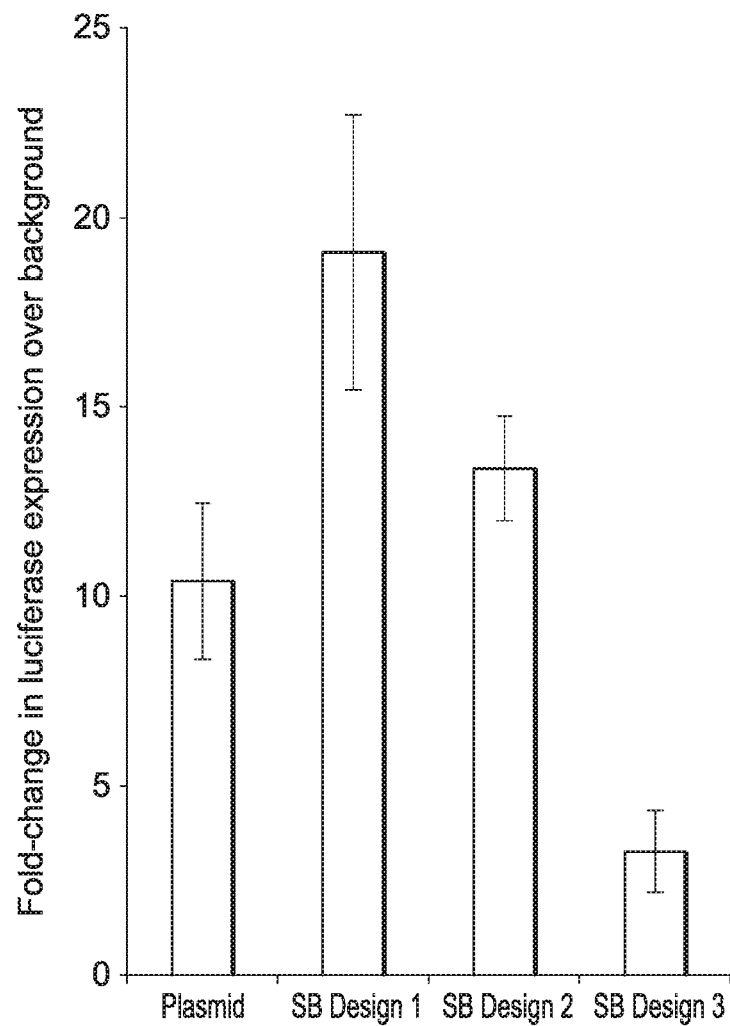
FIG. 5B shows luciferase expression levels achieved by different 1 cc DNA vectors provided by the present disclosure in NIH/3T3 fibroblasts. (See Examples 3 and 4.) Error bars indicate standard deviation across 2-3 replicate cultures.

FIG. 5B shows the luciferase expression levels achieved using three different luciferase-expressing 1 cc DNA vectors. As shown in FIG. 5B, transfection of all three 1 cc DNA vectors resulted in expression several-fold greater than background luciferase levels. Transfection of SB Design 1 or SB Design 2 1 cc DNA vectors resulted in robust expression levels exceeding that achieved with the pCMV-GLuc2 Control Plasmid.

These results demonstrated that the 1 cc DNA vectors were stable and capable of delivery a payload in an ex vivo cell line.

Example 5: Design and Production of Amplification Primers and Adaptor Oligonucleotides to Generate 1 cc DNA Vectors to Express a Secreted Embryonic Alkaline Phosphatase (SEAP) Reporter Gene The present Example demonstrates the design and primers and adaptor oligonucleotides suitable for use in disclosed methods of 1 cc DNA vectors.

Short (without an extension portion) and long (with an extension portion) primers were designed to anneal to a sequence within pSEAP2-Control plasmid (Clontech) (the "template").

Amplification primers having the nucleotide sequences shown below were synthesized, each containing a 5' phosphate. (Sequences are shown in the 5' to 3' direction.) Within depicted primer nucleotide sequences, lowercase letters indicate extension portions, and uppercase letter indicate portions complementary to the template.

SEAP_fwd_short:
(SEQ ID NO: 13)
TTA AGG TAC GGG AGG TAC TTG

SEAP_fwd_long:
(SEQ ID NO: 14)
tgt cgg tta gct cgc tca gct gat gTT AAG GTA CGG GAG GTA CTT G SEAP_rev_short:
(SEQ ID NO: 15)
TGG GTT GAA GGC TCT CAA G SEAP_rev_long:
(SEQ ID NO: 16)
ccc tat ggg tcg gcg caa tgc TGG GTT GAA GGC TCT CAA G Four different adaptors oligonucleotides were synthesized, each with a hairpin portion and an extension portion. The hairpin portions of each adaptor contained a double-stranded stem and a 9-base loop. The extension portions of each adaptor were complementary to or identical to the extension portions of the primers. Adaptor oligonucleotides were synthesized such that they each contained a 5' phosphate group. Nucleotide sequences of the adaptor oligonucleotides are shown below, with sequences in the 5' to 3' direction. Within depicted adaptor oligonucleotide sequences, lowercase letters indicate extension or hairpin loop portions, and uppercase letter indicate hairpin stem portions.

SB_SEAP_left_5':
(SEQ ID NO: 17)
cat cag ctg agc gag cta acc gac aCT GCG GTC AAC CTC AGG CGT AGA CCT CCt gta tgt tcG GAG GTC TAC GCC TGA GTT GGA CCG CAG SB_SEAP_left_3':
(SEQ ID NO: 18)
CAG CGC GCA ACA GCC TAC CTT CTC GGa cct atc taC CGA GAA GGT AGG CTG TTG CGC GCT Gtg tcg gtt agc tcg ctc agc tga tg SB_SEAP_right_5':
(SEQ ID NO: 19)
gca ttg cgc cga ccc ata ggg CTA ACG AAG GCG CCC GGT ACG GCA tta ccc atc TGC CGT ACC GGG CGC CTT CGT TAG SB_SEAP_right_3':
(SEQ ID NO: 20)
CGT CGG AGT GCG GAT CGA ACC TGG Cta agt agg tGC CAG GTT CGA TCC GCA CTC CGA CGc cct atg ggt cgg cgc aat gc Example 6: Production of 1 cc DNA SEAP Expression Vectors The present Example demonstrates that compositions and methods of the present disclosure can be used to generate linear covalently closed (1 cc) DNA vectors including a reporter gene.

A SEAP-expressing 1 cc DNA construct was generated as follows.

Amplification reactions were performed using pSEAP2-Control Plasmid (Clontech) as the template and primer pairs designed and described in Example 5. The primers used in the amplification reactions are indicated below:

1. Left extension reaction: SEAP_fwd_long & SEAP_rev_short
2. Right extension reaction: SEAP_fwd_short & SEAP_rev_long Amplification was carried out in 20 µL reactions using Herculase II Fusion DNA polymerase (Agilent Genomics). Each reaction contained 25 ng pSEAP2-Control, 250 nM of each primer, 1.5 M betaine, 250 µM each dNTPs, 1× Herculase II buffer, and 0.4 µL polymerase. Amplification reactions were carried out using the following thermal cycling conditions:
95° C. (2 minutes)
30 cycles of:
95° C. (15 seconds)
51° C. (20 seconds)
72° C. (5 min)
72° C.: (10 minutes)

Reaction products were purified using a Clean & Concentrator-25 kit (Zymo Research), using 10 mM Tris-Cl pH 8.5 as the elution buffer. Remaining primers were removed by digesting in a reaction of 70 µL containing 26-32 µg DNA and 20 U Exonuclease I (New England Biolabs) in 1× Exonuclease I buffer (6.7 mM MgCl$_2$, 10 mM β-mercaptoethanol, 67 mM glycine-KOH pH 9.5). Digestion reactions were incubated at 37° C. for 1 hour and heat-inactivated at 80° C. for 20 minutes. Desired products were purified using a Clean & Concentrator-25 kit (Zymo Research), using 10 mM Tris-Cl pH 8.5 as the elution buffer.

Thermal cycling ligation reactions were carried out in 50 µL reactions containing 5 µg left extension reaction products, an equimolar amount of right extension product, a 5× or 10× molar excess of each of the four adaptors described in Example 7 (SB_SEAP_left_5', SB_SEAP_left_3', SB_SEAP_right_5', and SB_SEAP_right_3') with respect to the total template concentration, 2U/µL Taq DNA Ligase (New England Biolabs), and 1× Taq DNA Ligase buffer (0.1% Triton X-100, 25 mM potassium acetate, 10 mM magnesium acetate, 1 mM NAD 1, 10 mM DTT, 20 mM Tris-HCl pH 7.6). The following thermal cycling conditions were used:
94° C. (2 minutes)
35 cycles of:
94° C. (15 seconds)
70° C. (30 minutes)
60° C.: (1 hour)

Ligation products were purified using a Clean & Concentrator-25 kit (Zymo Research) using 10 mM Tris-Cl pH 8.5 as the elution buffer.

To remove incompletely ligated fragments and parental plasmid DNA, the ligation products were digested in reactions consisting of 400 ng/µL, DNA, 0.1U/µL Dpn I (New England Biolabs), 0.45 U/µL T7 Exonuclease (New England Biolabs), and 1× CutSmart Buffer (10 ng/µL bovine serum albumin, 50 mM potassium acetate, 10 mM magnesium acetate, 20 mM Tris-acetate pH 7.9). Digests were carried out at 25° C. for 30 min and 37° C. for 15 minutes. DNA was purified using a Clean & Concentrator-25 kit (Zymo Research) using 10 mM Tris-Cl pH 8.5 as the elution buffer.

Assembled 1 cc DNA vectors had size of approximately 2.1 kb.

Concentrations of products were determined using agarose gel quantification. Yields of fully sealed vectors on the scale of approximately 100 µg were obtained.

These results provide further evidence that presently disclosed compositions and methods can be used produce robust yields of 1 cc nucleic acid vectors.

Example 7: In Vivo Expression of 1 cc DNA SEAP Expression Vectors

The present Example demonstrates that vectors provided by aspects of the disclosure can be successfully delivered to cells in an organism and expressed in vivo.

Figure 6:
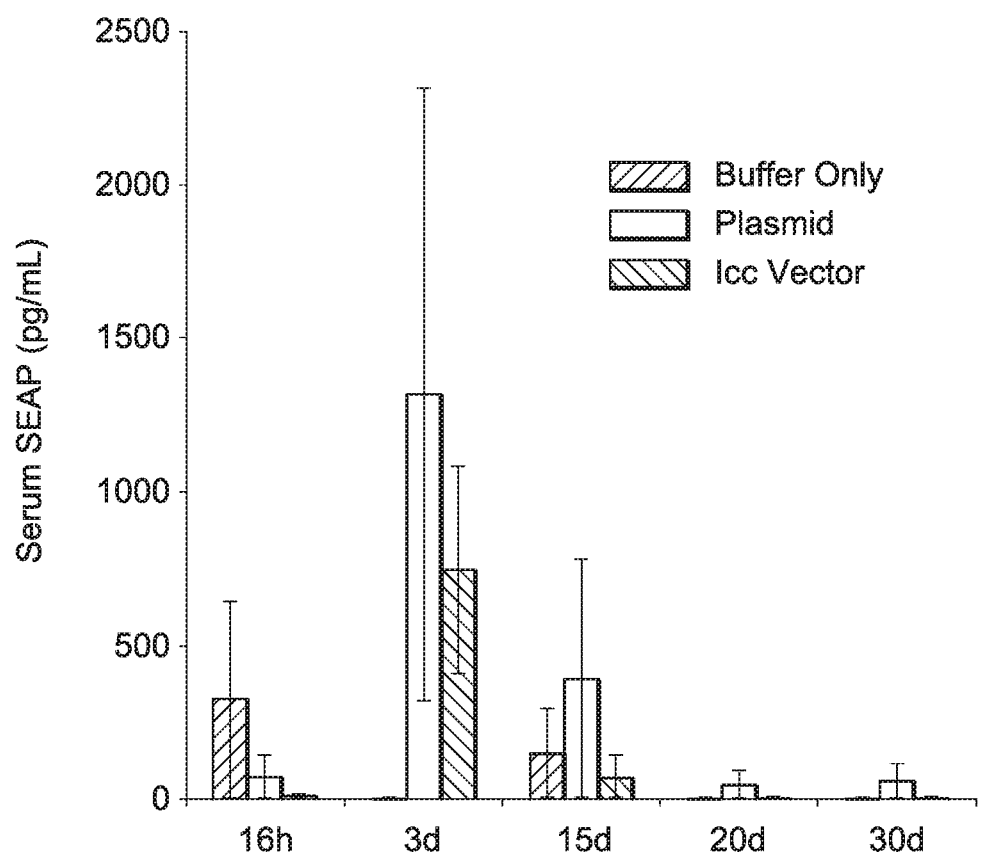
FIG. 6 shows SEAP serum levels at various times after intramuscular injection with equimolar amounts of plasmid or 1 cc DNA vectors of the present disclosure. (See Examples 5, 6, and 7.) Error bars indicate the range of observed values across 1-2 injected mice.

BALB/c 6-8 week-old males mice were anesthetized using isoflurane inhalation and injected with 6.1 μg 1 cc DNA SEAP expression vector (generated as described in Example 6) or an equimolar amount of pSEAP2-Control plasmid. Each mouse was injected with 50 μL of DNA in 1 mM Tris-Cl pH 8.5 into the tibias anterior muscle of one foot. Blood was collected via saphenous vein draws. Serum was isolated by centrifugation, and SEAP levels were measured using the Great EscAPe SEAP Chemiluminescence Kit 2.0 (Clontech). FIG. 6 shows the measured SEAP levels. As shown in FIG. 6 significant SEAP expression was observed with 1 cc DNA SEAP-expressing vectors as many as 15 days after intramuscular injection.

Other features of the invention will become apparent in the course of the following descriptions of exemplary embodiments, which are given for illustration of the invention and are not intended to be limiting thereof.

Exemplary Embodiments

Embodiment 1. A Composition Comprising:
(i) a first payload oligonucleotide including a first payload sequence and a first 3' extension sequence;
(ii) a second payload oligonucleotide including a second payload sequence and a second 3' extension sequence, wherein the first payload sequence is complementary to the second payload sequence;
(iii) a first adaptor oligonucleotide comprising:
  (a) a first stem sequence and a second stem sequence, wherein the first stem sequence is an inverted complement of the second stem sequence, and
  (b) a first adaptor 3' extension sequence that is complementary to the first 3' extension sequence; and
(iv) a second adaptor oligonucleotide comprising:
  (a) a third stem sequence and a fourth stem sequence, wherein the third stem sequence is an inverted complement of the fourth stem sequence, and
  (b) a second adaptor 3' extension sequence that is complementary to the second 3' extension sequence.

Embodiment 2. The composition of embodiment 1, wherein the first 5' extension sequence is 10 to 40 nucleotides in length.

Embodiment 3. The composition of embodiment 1 or 2, wherein the first adaptor 5' extension sequence is 10 to 40 nucleotides in length.

Embodiment 4. The composition of any one of embodiments 1-3, wherein the second 5' extension sequence is 10 to 40 nucleotides in length.

Embodiment 5. The composition of any one of embodiments 1-4, wherein the second adaptor 5' extension sequence is 10 to 40 nucleotides in length.The composition of embodiment 1, wherein the first 3' extension sequence is 10 to 40 nucleotides in length.

Embodiment 6. A composition comprising:
(i) a first payload oligonucleotide including a first payload sequence and a first 5' extension sequence;
(ii) a second payload oligonucleotide including a second payload sequence and a second 5' extension sequence, wherein the first payload sequence is complementary to the second payload sequence;
(iii) a first adaptor oligonucleotide comprising:
  (a) a first stem sequence and a second stem sequence, wherein the first stem sequence is an inverted complement of the second stem sequence, and
  (b) a first adaptor 5' extension sequence that is complementary to the first 5' extension sequence; and
(iv) a second adaptor oligonucleotide comprising:
  (a) a third stem sequence and a fourth stem sequence, wherein the third stem sequence is an inverted complement of the fourth stem sequence, and
  (b) a second adaptor 5' extension sequence that is complementary to the second 5' extension sequence.

Embodiment 7. The composition of embodiment 6, wherein the first 5' extension sequence is 10 to 40 nucleotides in length.

Embodiment 8. The composition of embodiment 6 or 7, wherein the first adaptor 3' extension sequence is 10 to 40 nucleotides in length.

Embodiment 9. The composition of any one of embodiments 6-8, wherein the second 3' extension sequence is 10 to 40 nucleotides in length.

Embodiment 10. The composition of any one of embodiments 6-9, wherein the second adaptor 3' extension sequence is 10 to 40 nucleotides in length.

Embodiment 11. The composition of any one of embodiments 1-10, wherein the composition comprises a molar excess of each of the first and second adaptor oligonucleotides relative to the first and second payload oligonucleotides.

Embodiment 12. The composition of embodiment 11, wherein the composition comprises at least a five-fold molar excess of at least one of the first and second adaptor oligonucleotides relative to the first and second payload oligonucleotides.

Embodiment 13. The composition of embodiment 11, wherein the composition comprises at least a five-fold molar excess of both the first and second adaptor oligonucleotides relative to the first and second payload oligonucleotides.

Embodiment 14. The composition of any one of embodiments 1-13, wherein the first and/or second adaptor oligonucleotides comprise a chemical modification.

Embodiment 15. The composition of embodiment 14, wherein the chemical modification is a modified nucleotide.

Embodiment 16. The composition of any one of embodiments 1-15, wherein the first and/or second adaptor oligonucleotides comprise a label.

Embodiment 17. The composition of any one of embodiments 1-16, wherein the first and/or second adaptor oligonucleotides are associated with a cell-penetrating peptide.

Embodiment 18. The composition of any one of embodiments 1-17, wherein the first and/or second adaptor oligonucleotides are associated with a polyamide.

Embodiment 19. The composition of any one of embodiments 1-18, wherein the first and/or second adaptor oligonucleotides are associated with an antigen-specific targeting ligand.

Embodiment 20. The composition of any one of embodiments 1-19, wherein the first and/or second adaptor oligonucleotides are associated with a nuclear localization sequence peptide.

Embodiment 21. The composition of any one of embodiments 1-20, wherein the first and/or second adaptor oligonucleotides include at least 20 nucleotides.

Embodiment 22. The composition of any one of embodiments 1-21, wherein:
(i) the first payload sequence is hybridized to the second payload sequence;
(ii) (a) the first adaptor 3' extension sequence is hybridized to the first 3' extension sequence or
(b) the first adaptor 5' extension sequence is hybridized to the first 5' extension sequence; and
(iii) (a) the second adaptor 3' extension sequence is hybridized to the second 3' extension sequence or
(b) the second adaptor 5' extension sequence is hybridized to the second 5' extension sequence.

Embodiment 23. The composition of any one of embodiments 1-22, wherein the first stem sequence and the second stem sequence are each 2 to 40 nucleotides in length.

Embodiment 24. The composition of any one of embodiments 1-23, wherein the third stem sequence and the fourth stem sequence are each 2 to 40 nucleotides in length.

Embodiment 25. The composition of any one of embodiments 1-24, wherein the first payload sequence and/or second payload sequence include an encoding region.

Embodiment 26. The composition of embodiment 25, wherein the encoding region encodes a gene product.

Embodiment 27. The composition of embodiment 26, wherein the gene product is an RNA or a polypeptide.

Embodiment 28. The composition of embodiment 25, wherein the encoding region encodes a fusion polypeptide or a chimeric polypeptide.

Embodiment 29. The composition of any one of embodiments 1-28, wherein the first payload sequence and/or second payload sequence include one or more regulatory elements.

Embodiment 30. The composition of embodiment 29, wherein the one or more regulatory elements are selected from the group consisting of a promoter, a transcriptional activator, an enhancer, a polyadenylation signal, a splice site, an internal ribosome entry site, a viral 2A element, and combinations thereof.

Embodiment 31. The composition of any one of embodiments 1-30, wherein the first payload sequence and/or second payload sequence are 50 nucleotides to 25,000 nucleotides in length.

Embodiment 32. The composition of any one of embodiments 1-31, wherein the first payload oligonucleotide further comprises a first 5' spacer and a first 3' spacer so that the first payload oligonucleotide includes in 5' to 3' order the first 5' extension sequence, the first 5' spacer, the first payload sequence, and the first 3' spacer.

Embodiment 33. The composition of embodiment 32, wherein the first 5' spacer and the first 3' spacer are each at least 10 nucleotides in length.

Embodiment 34. The composition of any one of embodiments 1-33, wherein the second payload oligonucleotide further comprises a second 5' spacer and a second 3' spacer so that the second payload oligonucleotide includes in 5' to 3' order the second 5' extension sequence, the second 5' spacer, the second payload sequence, and the second 3' spacer.

Embodiment 35. The composition of embodiment 34, wherein the second 5' spacer and the second 3' spacer are each at least 10 nucleotides in length.

Embodiment 36. The composition of any one of embodiments 1-35, wherein
(i) the first payload oligonucleotide further comprises a first 5' spacer and a first 3' spacer so that the first payload oligonucleotide includes in 5' to 3' order the first 5' extension sequence, the first 5' spacer, the first payload sequence, and the first 3' spacer; and
(ii) the second payload oligonucleotide further comprises a second 5' spacer and a second 3' spacer so that the second payload oligonucleotide includes in 5' to 3' order the second 5' extension sequence, the second 5' spacer, the second payload sequence, and the second 3' spacer;
wherein the first 5' spacer is complementary to the second 3' spacer and/or the first 3' spacer is complementary to the second 5' spacer.

Embodiment 37. A composition comprising:
(i) a first payload oligonucleotide including a first payload sequence and a first 3' extension sequence;
(ii) a second payload oligonucleotide including a second payload sequence and a second 3' extension sequence, wherein the first payload sequence is complementary to the second payload sequence;
(iii) a third payload oligonucleotide including the first payload sequence and a first 5' extension sequence;
(iv) a fourth payload oligonucleotide including the second payload sequence and a second 5' extension sequence;
(v) a first adaptor oligonucleotide comprising:
(a) a first stem sequence and a second stem sequence, wherein the first stem sequence is an inverted complement of the second stem sequence, and
(b) a first adaptor 3' extension sequence that is complementary to the first 3' extension sequence;
(vi) a second adaptor oligonucleotide comprising:
(a) a third stem sequence and a fourth stem sequence, wherein the third stem sequence is an inverted complement of the fourth stem sequence, and
(b) a second adaptor 3' extension sequence that is complementary to the second 3' extension sequence;
(vii) a third adaptor oligonucleotide comprising:
(a) a fifth stem sequence and a sixth stem sequence, wherein the fifth stem sequence is an inverted complement of the sixth stem sequence, and
(b) a first adaptor 5' extension sequence that is complementary to the first 5' extension sequence; and
(viii) a fourth adaptor oligonucleotide comprising:
(a) a seventh stem sequence and a eighth stem sequence, wherein the seventh stem sequence is an inverted complement of the eighth stem sequence, and
(b) a second adaptor 5' extension sequence that is complementary to the second 5' extension sequence.

Embodiment 38. The composition of any one of embodiments 1-37, further comprising a ligase.

Embodiment 39. The composition of embodiment 38, wherein the ligase is a temperature dependent ligase.

Embodiment 40. The composition of embodiment 38, wherein the ligase is a thermostable ligase.

Embodiment 41. The composition of any one of embodiments 1-40, wherein the first stem sequence is identical to the third stem sequence, and wherein the second stem sequence is identical to the fourth stem sequence.

Embodiment 42. A method of generating a linear covalently closed DNA vector comprising cycling the temperature of the composition according to any one of embodiments 38-40 through a first temperature and a second temperature, wherein the first temperature is higher than the second temperature.

Embodiment 43. The method of embodiment 42, wherein the temperature of the composition is cycled through the first temperature, the second temperature, and a third temperature, wherein the third temperature is within two degrees Celsius of an optimal temperature for the ligase.

Embodiment 44. The method of embodiment 43, wherein the third temperature is within 0.5 degrees Celsius of an optimal temperature for the ligase.

Embodiment 45. The method of any one of embodiments 42-44, wherein the temperature of the composition is cycled for 10-100 cycles.

Embodiment 46. Use of the composition of any one of embodiments 1-41 for the generation of a linear covalently closed DNA vector.

Embodiment 47. A method of generating a linear covalently closed DNA vector comprising:
  (i) performing a first amplification reaction on a first sample, thereby producing first amplification products, the first sample comprising:
    (a) at least one copy of a first single stranded nucleotide that includes a first payload sequence,
    (b) at least one copy of a second single stranded nucleotide that includes a second payload sequence, wherein the first payload sequence is complementary to the second payload sequence,
    (c) a first primer that includes a sequence complementary to a portion of the 5' end of the second payload sequence and a first extension sequence, and
    (d) a second primer that includes a sequence complementary to a portion of the 5' end of the first payload sequence;
  (ii) performing a second amplification reaction on a second sample, thereby producing second amplification products, the second sample comprising:
    (a) at least one copy of the first single stranded nucleotide that includes the first payload sequence,
    (b) at least one copy of the second single stranded nucleotide that includes a second payload sequence,
    (c) a third primer that includes a sequence complementary to a portion of the 5' end of the second payload sequence, and
    (d) a fourth primer that includes a sequence complementary to a portion of the 5' end of the first payload sequence and a second extension sequence;
  (iii) forming a composition comprising:
    (a) the first and second amplification products,
    (b) a set of adaptor oligonucleotides including:
      (1) a first adaptor oligonucleotide comprising:
        (aa) a first stem sequence and a second stem sequence, wherein the first stem sequence is an inverted complement of the second stem sequence, and
        (bb) a first adaptor 5' extension sequence that is complementary to the first extension sequence,
      (2) a second adaptor oligonucleotide comprising:
        (aa) a third stem sequence and a fourth stem sequence, wherein the third stem sequence is an inverted complement of the fourth stem sequence, and
        (bb) a second adaptor 5' extension sequence that is complementary to the second extension sequence,
      (3) a third adaptor oligonucleotide comprising:
        (aa) a fifth stem sequence and a sixth stem sequence, wherein the fifth stem sequence is an inverted complement of the sixth stem sequence, and
        (bb) a third adaptor 3' extension sequence that is the same as the first extension sequence, and
      (4) a fourth adaptor oligonucleotide comprising:
        (aa) a seventh stem sequence and an eighth stem sequence, wherein the seventh stem sequence is an inverted complement of the eighth stem sequence, and
        (bb) a fourth adaptor 3' extension sequence that is the same as the second extension sequence; and
    (c) a ligase; and
  (iv) cycling the temperature of a composition through a first temperature and a second temperature, wherein the first temperature is higher than the second temperature.

Embodiment 48. The method of embodiment 47, wherein the first and second primer of the first amplification reaction and the first and second primer of the second amplification reaction comprise a 5' phosphate.

Embodiment 49. The method of embodiment 47, further comprising contact the first and second amplification products with a kinase.

Embodiment 50. The method of any one of embodiments 47-49, further comprising a step of removing primers.

Embodiment 51. The method of embodiment 50, wherein the step of removing primers comprises using a purification column.

Embodiment 52. The method of embodiment 50 or 51, wherein the step of removing primers comprises incubating the first and/or second amplification products with a exonuclease.

Embodiment 53. The method of any one of embodiments 47-51, wherein the first stem sequence is identical to the fifth stem sequence, and wherein the second stem sequence is identical to the sixth stem sequence.

Embodiment 54. The method of any one of embodiments 47-53, wherein the third stem sequence is identical to the seventh stem sequence, and wherein the fourth stem sequence is identical to the eighth stem sequence.

Embodiment 55. A linear covalently closed DNA vector comprising:
  a single strand of DNA that includes:
    a first payload sequence;
    a second payload sequence hybridized to the first payload sequence;
    a first end region comprising a first stem sequence and a second stem sequence, wherein the first stem sequence is hybridized to the second stem sequence so that the first end region forms a hairpin, and wherein the 5' end of the first end region is covalently bound to the 3' end of the first payload sequence and the 3' end of the first end region is covalently bound to the 5' end of the second payload sequence; and
    a second end region comprising a third stem sequence and a fourth stem sequence, wherein the third stem sequence is hybridized to the fourth stem sequence so that the second end region forms a hairpin, and wherein the 5' end of the second end region is covalently bound to the 3' end of the second payload sequence and the 3' end of the second end region is covalently bound to the 5' end of the first payload sequence,
  wherein each of the first and the second end regions comprises an end of the linear covalently closed DNA vector, and
  wherein there are at least 30 nucleotides between each end and the closest 5' nucleotide of the first or second payload sequences to the respective end.

Embodiment 56. The linear covalently closed DNA vector of embodiment 55, wherein there are at least 40, 45, 50, 55, 60, 65, 70, 75, 80, 85, 90, 95, 100, 105, 110, 115, or 120 nucleotides between each end and the closest 5' nucleotide of the first or second payload sequences to the respective end.

Embodiment 57. The linear covalently closed DNA vector of embodiment 55, wherein the first payload sequence includes an encoding region between a gene regulatory element and a transcription terminator, wherein the first end region includes an end proximal to the gene regulatory element and the second end region includes an end proximal to the transcription terminator, wherein there are at least 30 nucleotides between the gene regulatory element and the end proximal to the gene regulatory element, and wherein there are at least 30 nucleotides between the transcription terminator and the end proximal to the transcription terminator.

Embodiment 58. The linear covalently closed DNA vector of embodiment 57, wherein there are at least 40, 45, 50, 55, 60, 65, 70, 75, 80, 85, 90, 95, 100, 105, 110, 115, or 120 nucleotides between the gene regulatory element and the end proximal to the gene regulatory element, and wherein there are at least 40, 45, 50, 55, 60, 65, 70, 75, 80, 85, 90, 95, 100, 105, 110, 115, or 120 nucleotides between the transcription terminator and the end proximal to the transcription terminator.

Embodiment 59. The linear covalently closed DNA vector of any one of embodiments 55-58, wherein the first and/or second end region comprises one or more chemical modifications.

Embodiment 60. The linear covalently closed DNA vector of embodiment 57, wherein the chemical modification comprises a modified nucleotide base.

Embodiment 61. The linear covalently closed DNA vector of any one of embodiments 55-60, wherein the first and/or second end region comprises a detectable label.

Embodiment 62. The linear covalently closed DNA vector of any one of embodiments 55-61, wherein the first and/or second end region is associated with a cell-penetrating peptide.

Embodiment 63. The linear covalently closed DNA vector of any one of embodiments 55-62, wherein the first and/or second end region is associated with a polyamide.

Embodiment 64. The linear covalently closed DNA vector of any one of embodiments 55-63, wherein the first and/or second end region is associated with an antigen-specific targeting ligand.

Embodiment 65. The linear covalently closed DNA vector of any one of embodiments 55-64, wherein the first and/or second end region is associated with a nuclear localization sequence peptide.

Embodiment 66. The linear covalently closed DNA vector of any one of embodiments 55-65, wherein the first and/or second end region is fully double-stranded.

Embodiment 67. The linear covalently closed DNA vector of any one of embodiments 55-66, wherein the first and/or second end region comprises a double-stranded portion and a single-stranded loop portion, wherein each single-stranded loop portion comprises an end of the linear covalently closed DNA vector.

EQUIVALENTS

Those skilled in the art will recognize, or be able to ascertain using no more than routine experimentation, many equivalents to the specific embodiments of the invention described herein.

The invention claimed is:

1. A method of generating a linear covalently closed DNA vector comprising:
   (i) performing a first amplification reaction on a first sample, thereby producing first amplification products, the first sample comprising:
      (a) at least one copy of a first single stranded polynucleotide that includes a first payload sequence,
      (b) at least one copy of a second single stranded polynucleotide that includes a second payload sequence, wherein the first payload sequence is complementary to the second payload sequence,
      (c) a first primer that includes a sequence complementary to a portion of the 5' end of the second payload sequence and one extension sequence, and
      (d) a second primer that includes a sequence complementary to a portion of the 5' end of the first payload sequence;
   (ii) performing a second amplification reaction on a second sample, thereby producing second amplification products, the second sample comprising:
      (a) at least one copy of the first single stranded polynucleotide that includes the first payload sequence,
      (b) at least one copy of the second single stranded polynucleotide that includes a second payload sequence,
      (c) a third primer that includes a sequence complementary to a portion of the 5' end of the second payload sequence, and
      (d) a fourth primer that includes a sequence complementary to a portion of the 5' end of the first payload sequence and one extension sequence;
   (iii) forming a composition comprising:
      (a) the first and second amplification products,
      (b) a set of adaptor oligonucleotides including:
         (1) a first adaptor oligonucleotide comprising:
            (aa) a first stem sequence and a second stem sequence, wherein the first stem sequence is an inverted complement of the second stem sequence, and
            (bb) a first adaptor 5' extension sequence that is complementary to the one extension sequence of the first primer,
         (2) a second adaptor oligonucleotide comprising:
            (aa) a third stem sequence and a fourth stem sequence, wherein the third stem sequence is an inverted complement of the fourth stem sequence, and
            (bb) a second adaptor 5' extension sequence that is complementary to the one extension sequence of the fourth primer,
         (3) a third adaptor oligonucleotide comprising:
            (aa) a fifth stem sequence and a sixth stem sequence, wherein the fifth stem sequence is an inverted complement of the sixth stem sequence, and
            (bb) a third adaptor 3' extension sequence that is the same as the one extension sequence of the first primer, and
         (4) a fourth adaptor oligonucleotide comprising:
            (aa) a seventh stem sequence and an eighth stem sequence, wherein the seventh stem sequence is an inverted complement of the eighth stem sequence, and
            (bb) a fourth adaptor 3' extension sequence that is the same as the one extension sequence of the fourth primer; and
      (c) a ligase; and
   (iv) cycling the temperature of the composition of step (iii) through a first temperature and a second temperature, wherein the first temperature is higher than the second temperature.

2. The method of claim 1, wherein the first and second primer of the first amplification reaction and the first and second primer of the second amplification reaction comprise a 5' phosphate.

3. The method of claim 1, further comprising contacting the first and second amplification products with a kinase.

4. The method of claim 1, further comprising a step of removing primers.

5. The method of claim 4, wherein the step of removing primers comprises using a purification column.

6. The method of claim 4, wherein the step of removing primers comprises incubating the first amplification product, the second amplification product, or both the first amplification product and the second amplification product with an exonuclease.

7. The method of claim 1, wherein the first stem sequence is identical to the fifth stem sequence, and wherein the second stem sequence is identical to the sixth stem sequence.

8. The method of claim 1, wherein the third stem sequence is identical to the seventh stem sequence, and wherein the fourth stem sequence is identical to the eighth stem sequence.

* * * * *